(12) United States Patent
Winter et al.

(10) Patent No.: US 11,408,407 B2
(45) Date of Patent: Aug. 9, 2022

(54) WOBBLE PLATE COMPRESSOR AND OXYGEN CONCENTRATOR USING THE SAME

(71) Applicant: CAIRE Inc., Ball Ground, GA (US)

(72) Inventors: David Phillip Winter, Encinitas, CA (US); Raziel Alon, Woodland Hills, CA (US); Gary Wayne Kozlow, San Marcos, CA (US)

(73) Assignee: CAIRE Inc., Ball Ground, GA (US)

( * ) Notice: Subject to any disclaimer, the term of this patent is extended or adjusted under 35 U.S.C. 154(b) by 351 days.

(21) Appl. No.: 15/659,344

(22) Filed: Jul. 25, 2017

(65) Prior Publication Data

US 2018/0023553 A1 Jan. 25, 2018

Related U.S. Application Data

(60) Provisional application No. 62/366,408, filed on Jul. 25, 2016.

(51) Int. Cl.
*F04B 27/08* (2006.01)
*F04B 27/18* (2006.01)
(Continued)

(52) U.S. Cl.
CPC ......... *F04B 27/086* (2013.01); *A61M 16/101* (2014.02); *F04B 27/1063* (2013.01); *F04B 27/12* (2013.01); *F04B 27/1804* (2013.01); *F04B 53/22* (2013.01); *B01D 53/0446* (2013.01); *B01D 2256/12* (2013.01); *B01D 2259/4533* (2013.01); *F04B 27/0886* (2013.01); *F04B 35/04* (2013.01)

(58) Field of Classification Search
CPC .......... F04B 1/16; F04B 27/12; F04B 27/086; F04B 27/1036; F04B 27/1054; F04B 27/1072; F04B 9/042; F04B 9/045; F04B 1/146; F01B 3/0005; F01B 3/02; F01B 3/04
USPC .................................................. 417/269–271
See application file for complete search history.

(56) References Cited

U.S. PATENT DOCUMENTS 1,367,914 A * 2/1921 Larsson ................ F01B 3/0023
91/160
3,181,475 A * 5/1965 Thompson ............ F04B 1/2042
91/502

(Continued)

FOREIGN PATENT DOCUMENTS

CA         1295305 C     2/1992
CN       87106684 A     4/1988
(Continued)

OTHER PUBLICATIONS

International Search Report and Written Opinon of Application No. PCT/US2017/043763 dated Dec. 21, 2017, 18 pgs.

(Continued)

*Primary Examiner* — Philip E Stimpert
(74) *Attorney, Agent, or Firm* — Leason Ellis LLP

(57) ABSTRACT

An oxygen concentrator includes a wobble plate compressor having one or more double-headed pistons and cylinders. A wobble plate of the compressor does not spin as an axle rotates, but orbitally tilts relative to the axle, thereby causing the double-headed pistons to move within the respective cylinders.

21 Claims, 25 Drawing Sheets

(51) Int. Cl.
*F04B 27/12* (2006.01)
*F04B 53/22* (2006.01)
*F04B 27/10* (2006.01)
*F04B 35/04* (2006.01)
*A61M 16/10* (2006.01)
*B01D 1/04* (2006.01)
*B01D 53/04* (2006.01)

(56) References Cited

U.S. PATENT DOCUMENTS

| | | | |
|---|---|---|---|
| 3,458,114 | A | 7/1969 | Catterson |
| 4,576,616 | A | 3/1986 | Mottram et al. |
| 4,826,474 | A | 5/1989 | Holmes |
| 5,593,291 | A | 1/1997 | Lynn |
| 5,593,478 | A | 1/1997 | Hill et al. |
| 5,699,715 | A * | 12/1997 | Forster ............... F04B 1/148 92/12.2 |
| 5,730,778 | A | 3/1998 | Hill et al. |
| 5,752,413 | A * | 5/1998 | Kuhn ............... F04B 1/146 417/269 |
| 6,074,174 | A | 6/2000 | Lynn et al. |
| 6,254,357 | B1 | 7/2001 | Lynn et al. |
| 6,540,777 | B2 | 4/2003 | Stenzel |
| 6,634,867 | B2 * | 10/2003 | Pressel ............... F04B 27/0878 417/269 |
| 6,733,248 | B2 | 5/2004 | Lynn |
| 7,302,883 | B2 | 12/2007 | Lynn et al. |
| 7,451,687 | B2 | 11/2008 | Lynn et al. |
| 7,455,008 | B2 | 11/2008 | Kurita et al. |
| 7,972,118 | B2 | 7/2011 | Hirabayashi et al. |
| 8,757,045 | B2 | 6/2014 | Terauchi |
| 8,783,161 | B2 | 7/2014 | Tagami |
| 8,997,631 | B2 | 4/2015 | Tagami |
| 9,046,089 | B2 | 6/2015 | Tagami |
| 2003/0072654 | A1 | 4/2003 | Pressel |
| 2003/0206811 | A1 * | 11/2003 | Maki ............... F04B 53/109 417/222.1 |
| 2005/0115401 | A1 | 6/2005 | Watanabe et al. |
| 2006/0230939 | A1 | 10/2006 | Bliss et al. |
| 2007/0081904 | A1 | 4/2007 | Kurita et al. |
| 2007/0101859 | A1 | 5/2007 | Nadamoto et al. |
| 2008/0075616 | A1 | 3/2008 | Rozek et al. |
| 2008/0304993 | A1 | 12/2008 | Lynn et al. |
| 2010/0071698 | A1 * | 3/2010 | Kiritake ............... A61M 16/009 128/205.27 |
| 2014/0128298 | A1 * | 5/2014 | Becker ............... C23C 14/021 508/107 |

FOREIGN PATENT DOCUMENTS

| | | |
|---|---|---|
| CN | 201486799 U | 5/2010 |
| CN | 203925924 U | 11/2014 |
| CN | 203978997 U | 12/2014 |
| GB | 1129801 A | 10/1968 |
| JP | S55148983 A | 11/1980 |
| JP | H0925872 A | 1/1997 |
| JP | 2001-507982 A | 6/2001 |
| KR | 20-1999-0032887 A | 7/1999 |
| KR | 100792497 B1 | 1/2008 |
| KR | 100803613 B1 | 2/2008 |
| KR | 10-2 010-0017660 A | 2/2010 |
| KR | 10-2014-0006938 | 1/2014 |
| WO | WO 98/29182 | 7/1998 |

OTHER PUBLICATIONS

Invitation to Pay Additional Fees and, Where Applicable, Protest Fee of Application No. PCT/US2017/043763 dated Oct. 25, 2017, 13 pgs.
First Chinese Office Action in corresponding Chinese Application No. 201780056258.5, dated Dec. 31, 2019 (an English translation attached hereto).
Third Chinese Office Action in corresponding Chinese Application No. 201780056258.5, dated Oct. 30, 2020 (an English translation attached hereto).
Office Action in corresponding Korean Application No. 2019-7002558, dated Jul. 22, 2021 (an English translation attached hereto).
Japanese Office Action in corresponding Japanese Application No. 2019-503671 dated Jul. 1, 2021 (an English translation attached hereto).
Second Chinese Office Action in corresponding Chinese Application No. 201780056258.5, dated Jul. 14, 2020 (an English translation attached hereto).
Office Action in corresponding Chinese Application No. 201780056258.5, dated Apr. 2, 2021 (an English translation attached hereto).

* cited by examiner

WOBBLE PLATE COMPRESSOR AND OXYGEN CONCENTRATOR USING THE SAME

CROSS-REFERENCE TO RELATED APPLICATION(S)

This application claims the benefit of U.S. Patent Application Ser. No. 62/366,408 titled WOBBLE PLATE COMPRESSOR AND OXYGEN CONCENTRATOR USING THE SAME filed Jul. 25, 2016, the disclosure of which is hereby incorporated by reference in its entirety.

BACKGROUND

Portable oxygen concentrators are commonly used in the home medical market to treat ambulatory patients with chronic obstructive pulmonary diseases. To make an oxygen concentrator portable, the oxygen concentrator must be as small as possible and weigh as little as possible while delivering sufficient concentrated oxygen gas flow to the ambulatory patient.

Oxygen concentrators use compressors to supply high-pressure feed air to a concentrator. Compressors typically use viscous lubricant or oil. Such lubricant or oil can contaminate the air flow path in the concentrator. Further, compressors in the oxygen concentrators can produce a significant amount of vibration and noise during use, making it unsuitable for portable concentrators. It is therefore desirable for compressors to run oil-less with reduced noise, vibration, and weight while providing required vacuum/pressure levels and flow rates with less power consumption.

Wobble Plate Compressor and Oxygen Concentrator

In general terms, this disclosure is directed to a wobble plate compressor and an oxygen concentrator using the compressor. In one possible configuration and by non-limiting example, the compressor includes a wobble plate associated with double-headed pistons. Various aspects are described in this disclosure, which include, but are not limited to, the following aspects.

One aspect is a wobble plate compressor including a motor, a wobble plate, a double-headed piston assembly, and at least one single-piece cylinder. The motor rotates an axle around an axis of rotation. The wobble plate has at least one distal attachment member and is coupled to the axle so that the distal attachment member reciprocates upon rotation of the axle. The single-piece cylinder receives the double-headed piston assembly to define two compression chambers. The cylinder includes a window through which the wobble plate engages with the piston assembly such that the distal attachment member penetrates the piston assembly whereby the piston assembly reciprocates within the cylinder along a second axis parallel to the axis of rotation upon rotation of the axle and the distal attachment member reciprocates generally in an axial path along the second axis.

Another aspect is an oxygen concentrator including a concentrator and a wobble plate compressor. The compressor includes a motor that rotates an axle around an axis of rotation; a wobble plate having at least two balls, each ball on a different distal portion of the wobble plate, the wobble plate coupled to the axle so that each ball reciprocates upon rotation of the axle; a double-headed piston; and at least one single-piece cylinder receiving the double-headed piston assembly to define two compression chambers, the cylinder including a window through which the wobble plate engages with the piston assembly such that the piston is attached to an associated one of the balls whereby the piston reciprocates within the cylinder upon the rotation of the axle and the ball reciprocates generally in an axial path along an axis of the cylinder.

Yet another aspect is a method of assembling a wobble plate with a piston assembly. The wobble plate includes at least one distal attachment member, and the piston assembly includes a piston head and at least one connecting rod. The method includes mounting a first magnetic element to the at least one connecting rod; arranging an assembly tool adjacent the piston head at a predetermined location, the assembly tool including a second magnetic element configured to magnetically attract the first magnetic element of the at least one connecting rod to bias the at least one connecting rod to a predetermined position when the assembly tool is arranged adjacent the piston head at the predetermined location; engaging the at least one distal attachment member with the at least one connecting rod; and removing the assembly tool from the piston head.

DETAILED DESCRIPTION

Figure 1:
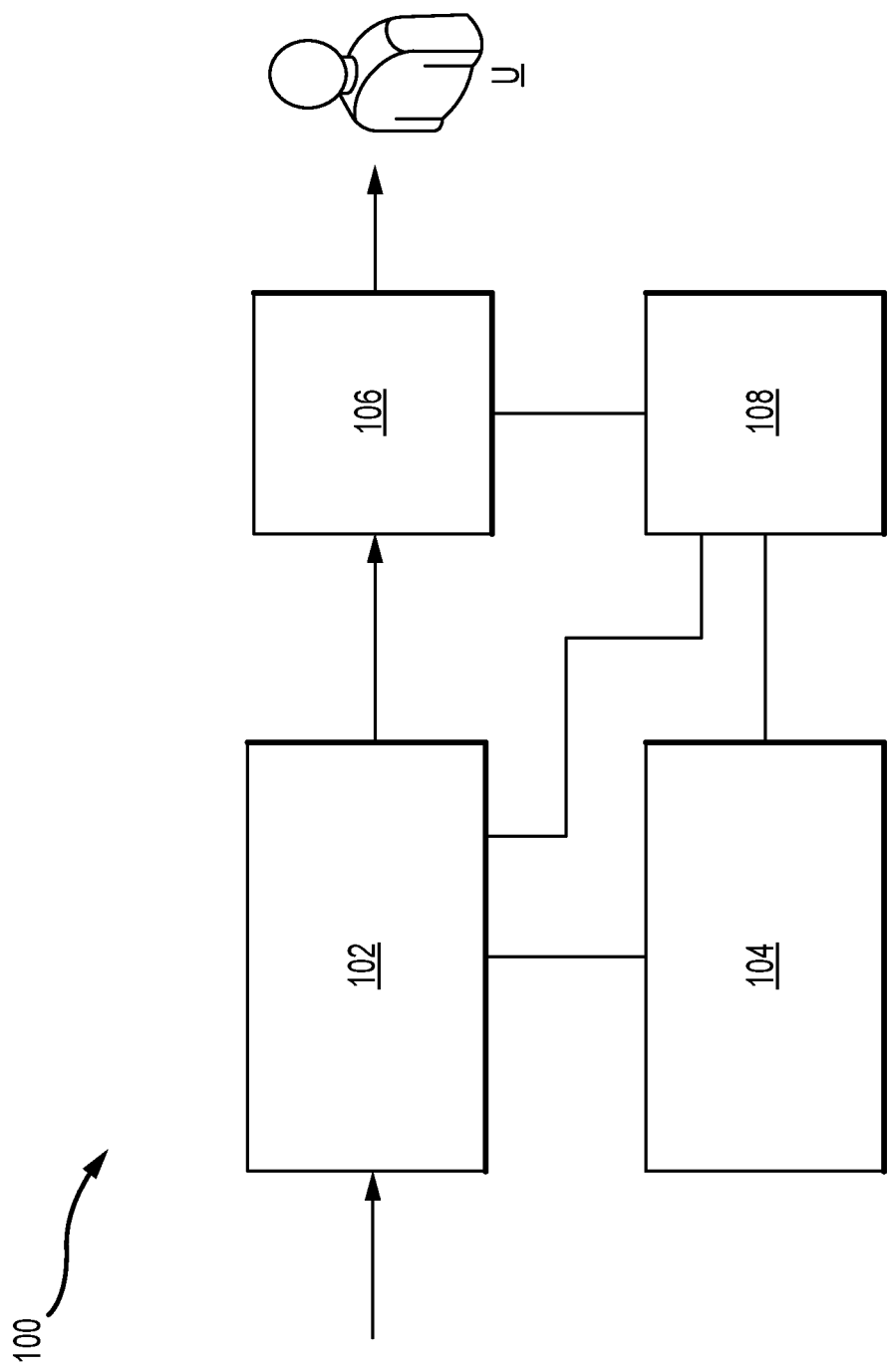
FIG. 1 is a block diagram of an oxygen concentration system in accordance with an exemplary embodiment of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

In general, in accordance with the present disclosure, an oxygen concentrator includes a wobble plate compressor having one or more double-headed cylinders. In certain examples, an oxygen concentrator uses a wobble plate compressor design with double-headed pistons. The wobble plate is attached to an axle at an angle so as to be orbitally tilted around an axis of rotation of the axle. The wobble plate does not spin as the axle rotates, but changes the angular orientation of the fixed tilt of the wobble plate with respect to the axle, thereby causing the double-headed pistons to move within the respective cylinders. The wobble plate compressor is configured as a dry system, which does not require viscous lubricant (e.g., oil or grease), for both pressurizing air and drawing a vacuum for use in a portable oxygen concentrator. It is a portable, low noise, low vibration, low power combination vacuum and pressure pump.

The wobble plate sub-assembly may have bearing grade steel balls connected to pins. The pins are connected to the central hub of the wobble plate. A bearing, such as a ball bearing or a thrust bearing, is disposed between the hub and the axle (i.e., drive shaft). Each piston is driven axially within the cylinder associated with the piston, by one or two tibias (also referred to herein as connecting rods or piston rods) that spherically mate with the ball at one end, and spherically mate with the piston at the opposite end. The piston outer diameter may be coated with low-friction wear barrier paint. The tibias move slightly off-axis to accommodate the non-axial motion of the ball within the cylinder. Any number of cylinders can be arranged in a circle from the drive shaft that is coincident with the power shaft. In some examples, the cylinders are arranged equidistant from the drive shaft. When the drive shaft rotates, the hub does not spin since its bearing isolates the hub and the drive shaft. Instead, the hub wobbles as dictated by the drive shaft's angle. In some examples, a constant velocity (CV) joint is provided to prevent rotational torque on the hub. The CV joint can be integrated with the hub with the CV shaft flexibly attaching to a grounded item such as the manifold. The CV joint can reduce the drag torque that the pistons would otherwise bear with flank loads on the cylinders. As such, the CV joint can eliminate the friction at the pistons and thereby improve energy efficiency to the overall arrangement.

The two manifolds capture the cylinders therebetween. In some cases, the manifolds are mirrors of each other so opposing cylinder heads perform the same function but 180 degrees out of phase. One example of the compressor has one cylinder (two heads) producing positive pressure flow and two cylinders (four heads) producing negative pressure flow. A shroud may be formed to force cooling gases through the compressor. Such internal cooling reduces the system package size.

FIG. 1 is a block diagram of an oxygen concentration system 100 in accordance with an exemplary embodiment of the present disclosure. In some examples, the oxygen concentration system 100 is a portable oxygen concentration system. The oxygen concentration system 100 includes a gas separation device 102, an energy source 104, one or more output sensors 106, and a control unit 108.

The gas separation device 102 operates to separate concentrated oxygen gas from ambient air. An example of the gas separation device 102 is an oxygen gas generator. In this document, the gas separation device 102 is also referred to as the air separation device or the oxygen gas generator 102. The energy source 104 powers at least a portion of the oxygen gas generator 102. Examples of the energy source 104 include rechargeable battery, battery pack, and fuel cell. The output sensors 106 are used to sense one or more conditions, such as conditions of a user U and the environment, to determine the oxygen output needed by the user or required from the system 100. The control unit 108 is linked to the output sensors 106, the air separation device 102, and the energy source 104 to control the operation of the air separation device 102 in response to the one or more conditions sensed by the one or more output sensors 106.

In an alternative embodiment, the system 100 does not include the one or more output sensors 106 coupled to the control unit 108. In this embodiment, conditions of the system 100 such as flow rate, oxygen concentration level, etc. may be constant for the system or may be manually controllable. For example, the system 100 may include a user interface that allows the user, provider, doctor, etc. to enter information, e.g., prescription oxygen level, flow rate, etc. to control the oxygen output of the system 100.

Figure 2:
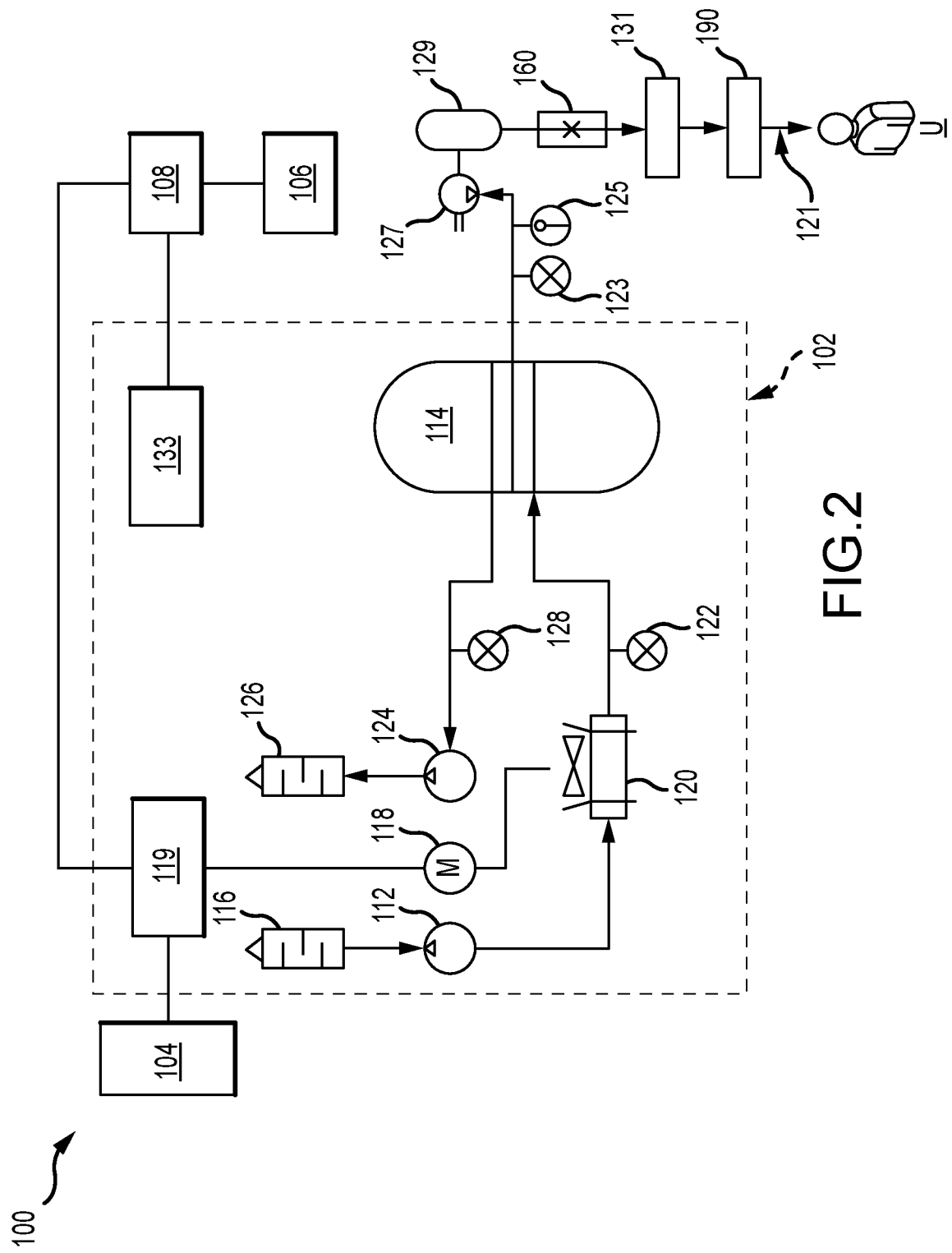
FIG. 2 is a block diagram of an exemplary embodiment of a gas separation device.

FIG. 2 is a block diagram of an exemplary embodiment of the gas separation device 102. The gas separation device 102 includes a pump such as a compressor 112 and an oxygen concentrator 114, which, in some examples, are integrated.

As illustrated, the gas separation device 102 includes one or more of the elements shown within the segmented boundary line in FIG. 2. Ambient air is drawn through an inlet muffler 116 by the compressor 112. In some examples, the muffler 116 is integrated with the compressor 112, as described below. The compressor 112 may be driven by one or more DC motors 118 that run off of DC electrical current supplied by the energy source 104 (e.g., rechargeable battery). The motor 118 can also drive the cooling fan part of a heat exchanger 120. A variable-speed controller or compressor motor speed controller 119 may be integral with or separate from the control unit 108 and is preferably coupled to the motor 118 for conserving electricity consumption. The compressor 112 delivers the air under pressure to the concentrator 114.

A heat exchanger 120 may be located between the compressor 112 and the concentrator 114 to cool or heat the air to a desired temperature before entering the concentrator 114. A filter (not shown) may be located between the compressor 112 and the concentrator 114 to remove any impurities from the supply air. A pressure transducer 122 may be located between the compressor 112 and the concentrator 114 to get a pressure reading of the air flow entering the concentrator 114.

The concentrator 114 separates oxygen gas from air for eventual delivery to the user in a well-known manner. One or more of the following components may be located in a supply line 121 between the concentrator 114 and the user: a pressure sensor 123, a temperature sensor 125, a pump 127, a low-pressure reservoir 129, a supply valve 160, a flow and purity sensor 131, and a conservation device 190. As used herein, the supply line 121 refers to the tubing, connectors, or any other elements used to connect the components in the line. The pump 127 may be driven by the motor 118. The oxygen gas may be stored in the low-pressure reservoir 129 and delivered therefrom via the supply line 121 to the user. The supply valve 160 may be used to control the delivery of oxygen gas from the low-pressure reservoir 129 to the user at atmospheric pressure.

Exhaust gas may also be dispelled from the concentrator 114. In some examples, a vacuum generator 124, which may also be driven by the motor 118 and integrated with the compressor 112, draws exhaust gas from the concentrator 114 to improve the recovery and productivity of the concentrator 114. The exhaust gas may exit the system 100 through an exhaust muffler 126. A pressure transducer 128 may be located between the concentrator 114 and the vacuum generator 124 to get a pressure reading of the exhaust flow from the concentrator 114.

The variable-speed controller 119 reduces the power consumption requirements of the compressor 112 on the energy source 104 (e.g., a rechargeable battery 104). With the variable-speed controller 119, the speed of the compressor 112 may be varied with the activity level of the user, metabolic condition of the user, environmental condition, or other condition indicative of the oxygen needs of the user as determined through the one or more output sensors 106. For example, the variable-speed controller may decrease the speed of the motor 118 when it is determined that the oxygen requirements of the user are relatively low, e.g., when the user is sitting, sleeping, at lower elevations, etc., and increased when it is determined that the oxygen requirements of the user are relatively high or higher, e.g., when the user stands, when the user is active, when the user is at higher elevations, etc. This helps to conserve the life of the battery 104, reduce the weight and size of the battery 104, and reduce the compressor wear rate, improving its reliability. An example of the variable-speed controller, which regulates the compressor speed to operate the compressor only at the speed and power needed to deliver oxygen at the user's prescribed flow rate, is disclosed in U.S. Pat. Nos. 5,593,478 and 5,730,778, the entireties of which are hereby incorporated by reference.

Referring still to FIG. 2, the concentrator 114 is configured to implement one or more processes, such as a pressure swing adsorption (PSA) process, a vacuum pressure swing adsorption (VPSA) process, a rapid PSA process, a very rapid PSA process, a vacuum swing adsorption (VSA) process, and/or other processes.

In some examples, the oxygen gas generator 102 also includes an oxygen source in addition to the concentrator 114 such as, but not by way of limitation, a high-pressure oxygen reservoir. Further, a valve controller 133 may be integral with or separate from the control unit 108 and is coupled with valve electronics in the concentrator 114 for controlling the valve(s) of the concentrator 114.

Although the concentrator 114 is primarily described as separating oxygen from air, it should be noted that the concentrator 114 may be used for other applications such as, but not by way of limitation, air separations for the production of nitrogen, hydrogen purification, water removal from air, and argon concentration from air. As used herein, the term "fluids" includes both gases and liquids.

Figure 3:
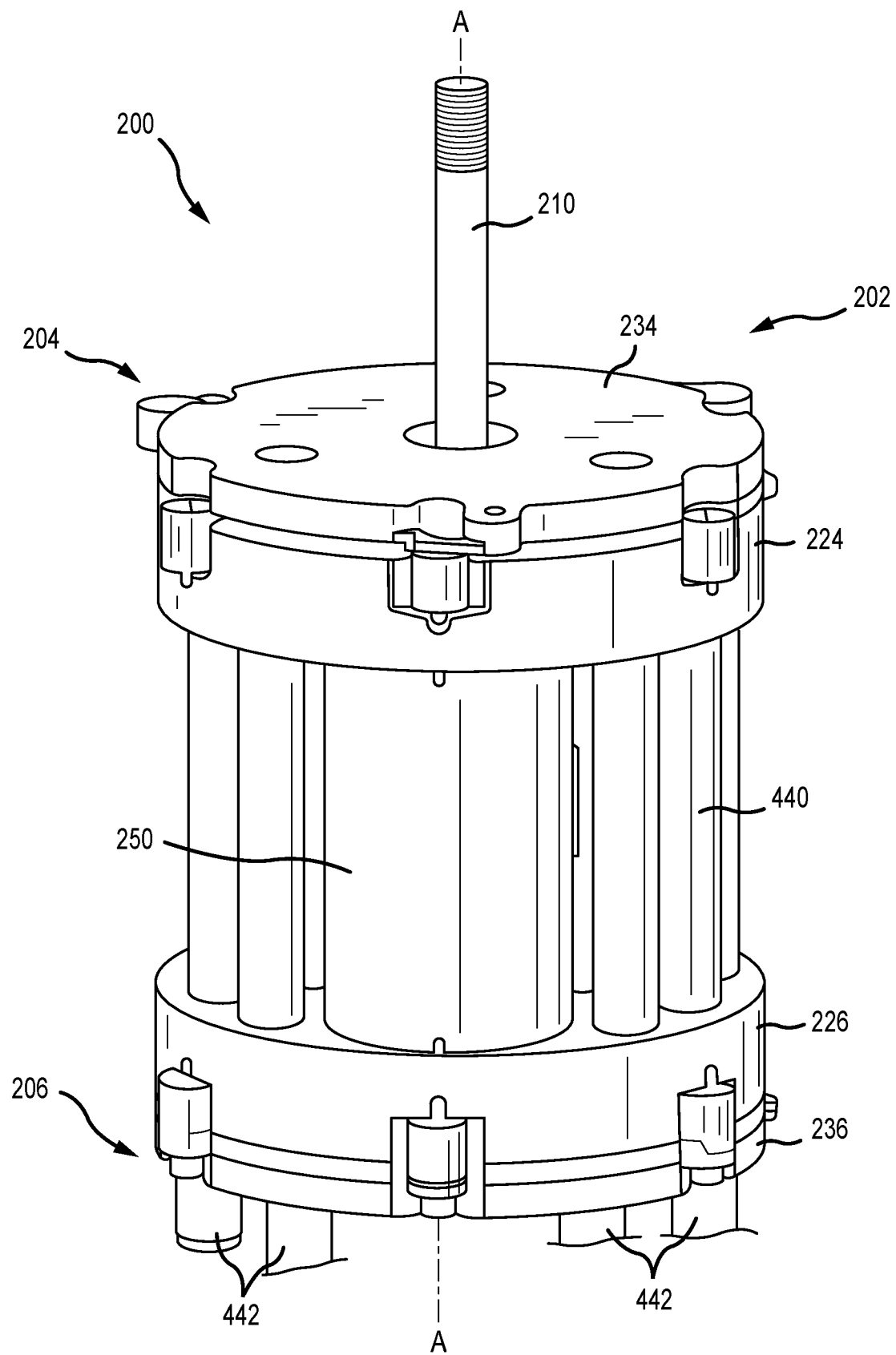
FIG. 3 schematically illustrates an example compressor.
Figure 4:
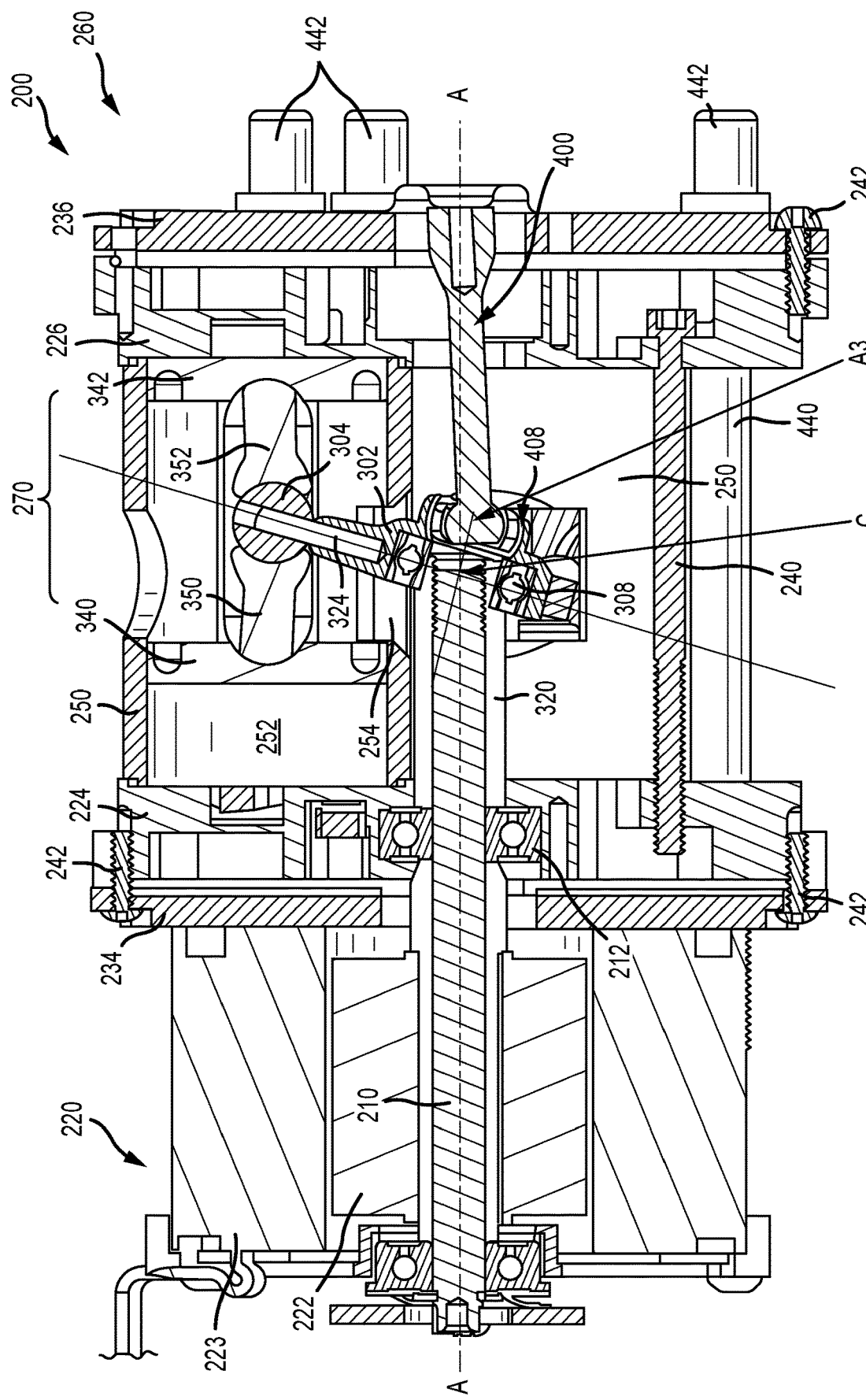
FIG. 4 is a cross sectional view of the compressor of FIG. 3.

Referring to FIGS. 3 and 4, a compressor 200 in accordance with an exemplary embodiment of the present disclosure is generally described. In particular, FIG. 3 schematically illustrates an example compressor 200, and FIG. 4 is a cross sectional view of the compressor 200.

In general, the compressor 200 in accordance with the present disclosure is a wobble plate compressor, which operates to compress and evacuate air and other gases particularly to and from the gas separation device 102. As described below, the compressor 200 of the present disclosure is configured to be interchangeably used, with or without modification, for various types of gas separation devices, such as pressure swing gas separation devices, vacuum swing gas separation devices, pressure-vacuum swing gas separation devices, and any suitable gas separation devices.

In this document, it is primarily described that the compressor 200 is used with the oxygen concentrator. In other examples, however, the compressor 200 of the present disclosure can be used with or as part of any respiratory care equipment. In yet other examples, the compressor 200 of the present disclosure can also be used for any purposes where compressed gas or vacuum is needed.

In the illustrated example, the compressor 200 is configured for a small pressure-vacuum swing compressor system. For example, the compressor 200 may correspond to the compressor 112 integrated with the vacuum generator 124, as described in FIG. 2. As described below, the compressor 200 provides a six-head variety that is implemented by three double-sided pistons within three cylinders.

The compressor 200 is configured for compressible gases that need to be free of viscous lubricants, such as oil or grease, which would otherwise enter the air flow path, for example. At least part of the output from the compressor 200 is delivered to the gas separation device that separates oxygen from air. The oxygen is then output for medical or other purposes. Absence of viscous lubricants therefore helps improve quality of the oxygen output from the gas separation device.

Referring to FIG. 3, the compressor 200 includes a housing 202 that contains and/or supports various components of the compressor 200. The housing 202 generally extends between a first end 204 and a second end 206 along an axis of rotation A, about which a drive shaft 210 (also referred to herein as an axle) is rotated. As shown in FIG. 4, the drive shaft 210 is driven by a motor 220. In some examples, the housing 202 includes a first manifold 224 arranged at the first end 204 and a second manifold 226 arranged at the second end 206 and spaced apart from the first manifold 224. The first manifold 224 and the second manifold 226 define opposing end faces, between which one or more cylinders 250, a wobble plate assembly 260, one or more piston assemblies 270, and other associated components are disposed. In some examples, the first manifold 224 and the second manifold 226 are tightened together using one or more fasteners 240, which longitudinally extends between the first and second manifolds 224 and 226 (FIG. 4). The first manifold 224 and the second manifold 226 are described in more detail with reference to FIGS. 11-13.

In some examples, the housing 202 further includes a first cover 234 adapted to cover an end surface of the first manifold 224 at the first end 204, and a second cover 236 adapted to cover an end surface of the second manifold 226 at the second end 206. The first cover 234 and the second cover 236 are attached to the first manifold 224 and the second manifold 226 in various manners. In the illustrated example, the first cover 234 and the second cover 236 are fastened to the first manifold 224 and the second manifold 226, respectively, by fasteners (e.g., screws 242 (FIG. 4)). In other examples, the first cover 234 and the first manifold 224 are integrally formed, and the second cover 236 and the second manifold 226 are integrally formed.

Although it is primarily described in the present disclosure that the first manifold 224, the second manifold 226, the first cover 234, the second cover 236, the cylinders 250, and other associated components are separately formed and coupled to one another to constitute the housing 202, the housing 202 may be integrally formed to provide at least some or all of the first manifold 224, the second manifold 226, the first cover 234, the second cover 236, the cylinders 250, and other non-moving components.

Referring to FIG. 4, the compressor 200 includes one or more cylinders 250, a wobble plate assembly 260, and one or more piston assemblies 270.

The compressor 200 may include a plurality of cylinders 250. In some examples, the cylinder 250 includes at least one pressure cylinder and at least one vacuum cylinder. The number of cylinders 250 can vary for various purposes. In some examples, the compressor 200 includes an odd number of cylinders 250 for the purpose of reducing torque spikes and noise since no two pistons reach top head center at the same time. The number of cylinders 250 may also be selected to affect a predetermined ratio of positive pressure flow to negative pressure flow. In some configurations, such negative pressure is considered to be lower than atmospheric pressure. The ratio is then used to optimize efficiency of the gas separation device to which the compressor 200 supports.

Figure 7:
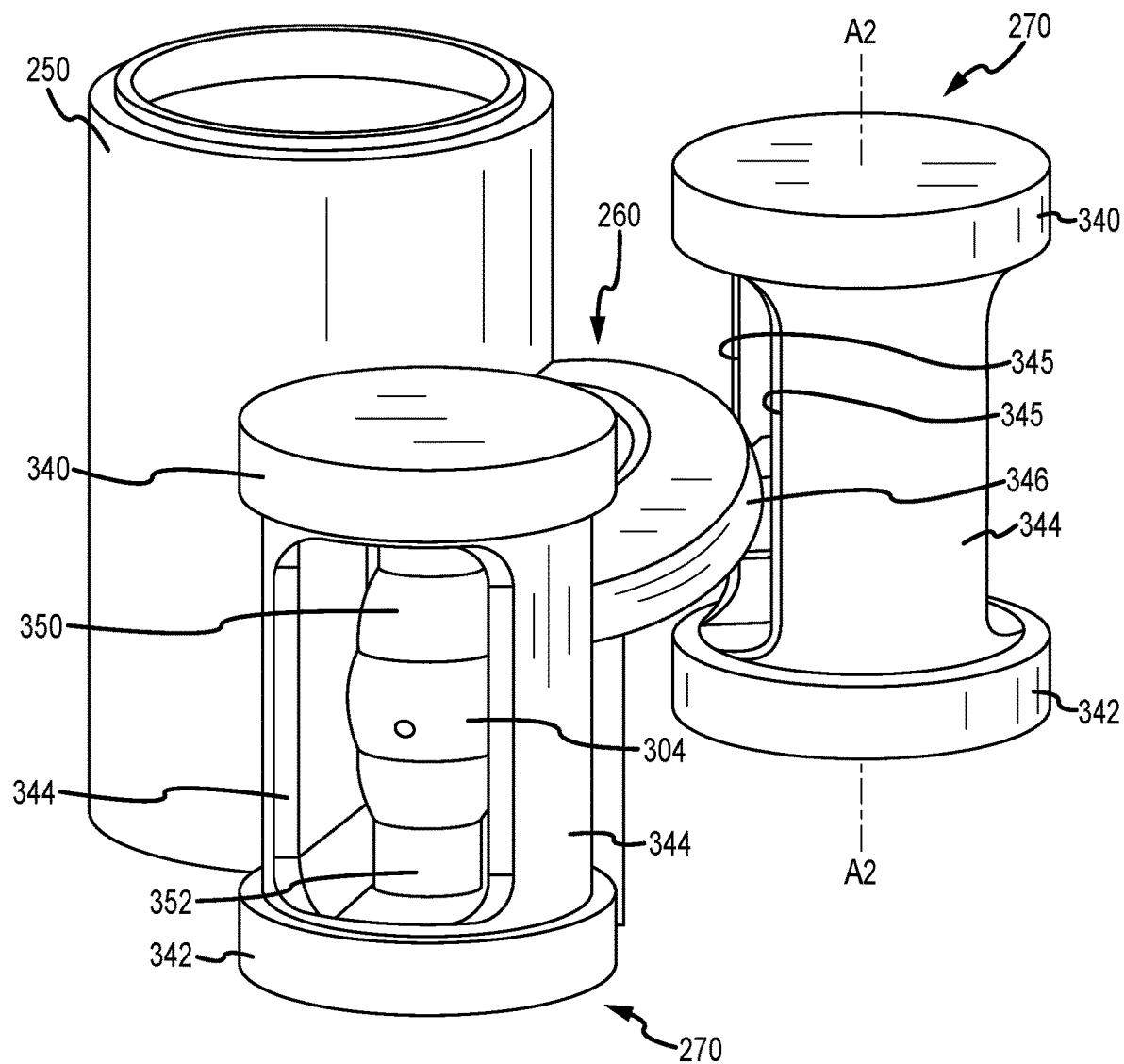
FIG. 7 schematically illustrates example piston assemblies coupled to the wobble plate assembly.
Figure 13:
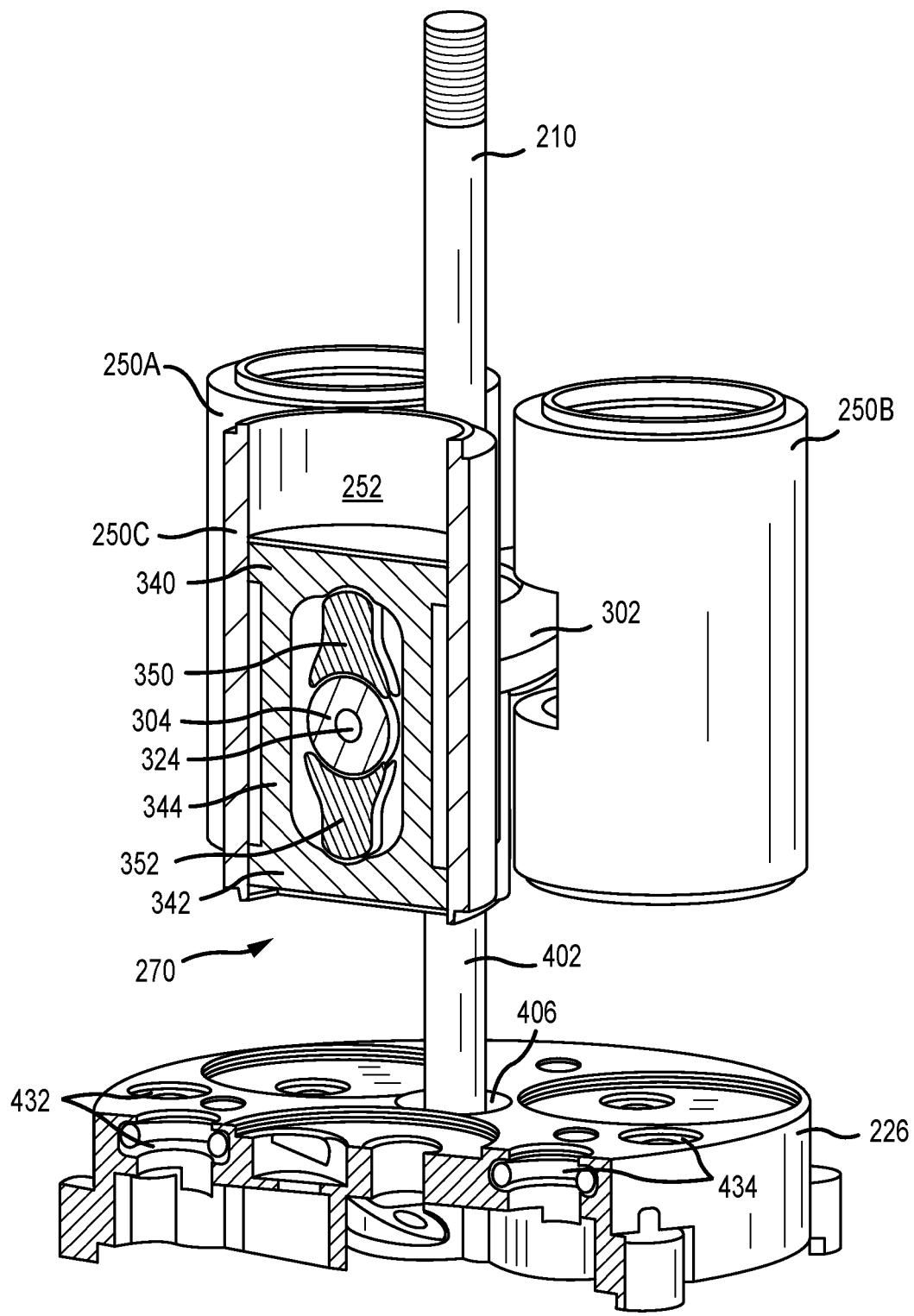
FIG. 13 schematically illustrates the second manifold connected to the wobble plate assembly, which is coupled to the piston assemblies contained within respective cylinders.

In the illustrated example, the compressor 200 includes three cylinders 250, as shown in FIGS. 7 and 13, which consist of one cylinder for positive pressure flow (i.e., a positive pressure cylinder or a pressure cylinder 250A) and two cylinders for negative pressure flow (i.e., a first negative pressure cylinder or a first vacuum cylinder 250B and a second negative pressure cylinder or a second vacuum cylinder 250C). In this configuration, therefore, the compressor 200 can operate two compression chambers in pressure (with the one pressure cylinder 250A) and four compression chambers in vacuum (with the two vacuum cylinders 250B and 250C). In other examples, other configurations are possible.

In some examples, two compression chambers that are defined in each of the cylinders 250 can be used for the same function, such as either for positive pressure flow or for negative pressure flow. In other examples, two compression chambers in each of the cylinders 250 can be used for different functions, such as one of the compression chambers being used for positive pressure flow and the other compression chamber being used for negative pressure flow.

In the illustrated example, the cylinders 250 are equally spaced from the axis of rotation A of the drive shaft. In other examples, at least one of the cylinders 250 can be spaced from the axis of rotation of the drive shaft at a different distance than the other cylinder(s) 250, such that the pistons of the cylinders 250 can have different strokes.

The cylinders 250 are disposed between the first and second manifolds 224 and 226 such that the first and second manifolds 224 define chambers 252 within the cylinders 250. The cylinders 250 have inner diameters that are finely machined and sized to movably receive the piston assemblies 270 therein. The cylinders 250 can be made of various materials, such as metal (e.g., aluminum) and other suitable materials.

Referring still to FIG. 4, the drive shaft 210 extends through the first manifold 224 and the first cover 234 and rotates about the axis of rotation A. One end of the drive shaft 210 is operatively coupled to the wobble plate assembly 260, as described in more detail below. The drive shaft 210 is driven by a motor 220 and rotatably supported by the housing 202. In the illustrated example, the drive shaft 210 is journaled by a bearing 212 to the first manifold 224 of the housing 202.

In the illustrated example, the motor 220 includes a stator 223 fixed to the first cover 234 of the compressor 200, and a rotor 222 that is fitted around a portion of the drive shaft 210. In some example, the motor 220 is used as the motor 118 as described in FIG. 2.

Figure 5:
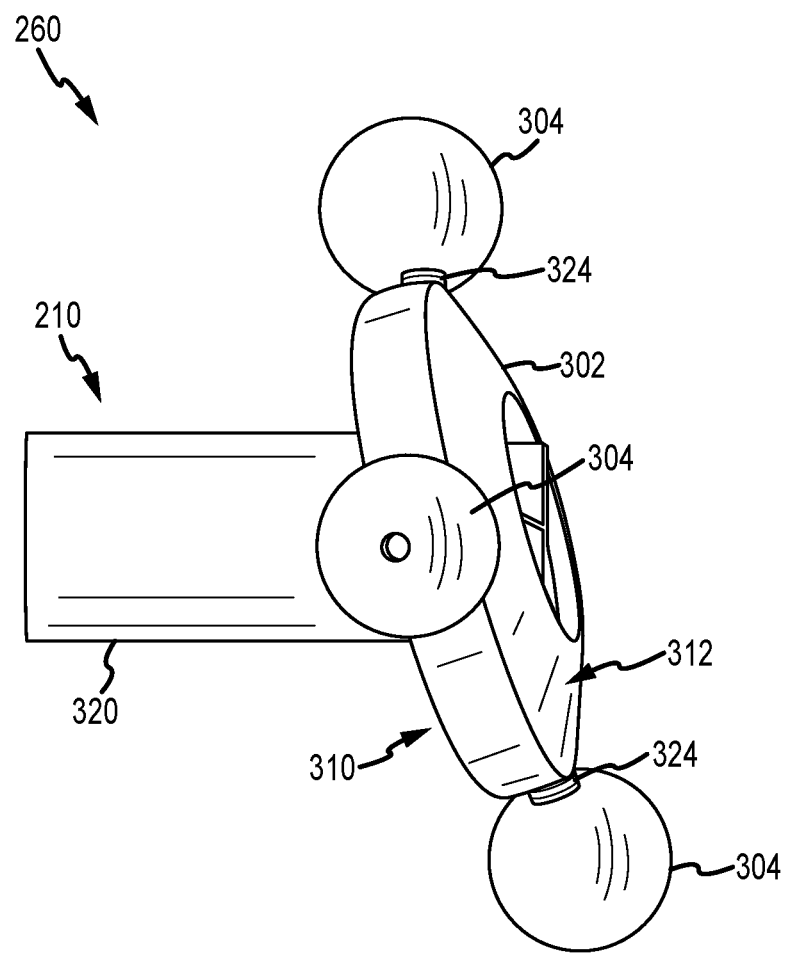
FIG. 5 is a schematic side view of a wobble plate assembly coupled to an end of a drive shaft.
Figure 6:
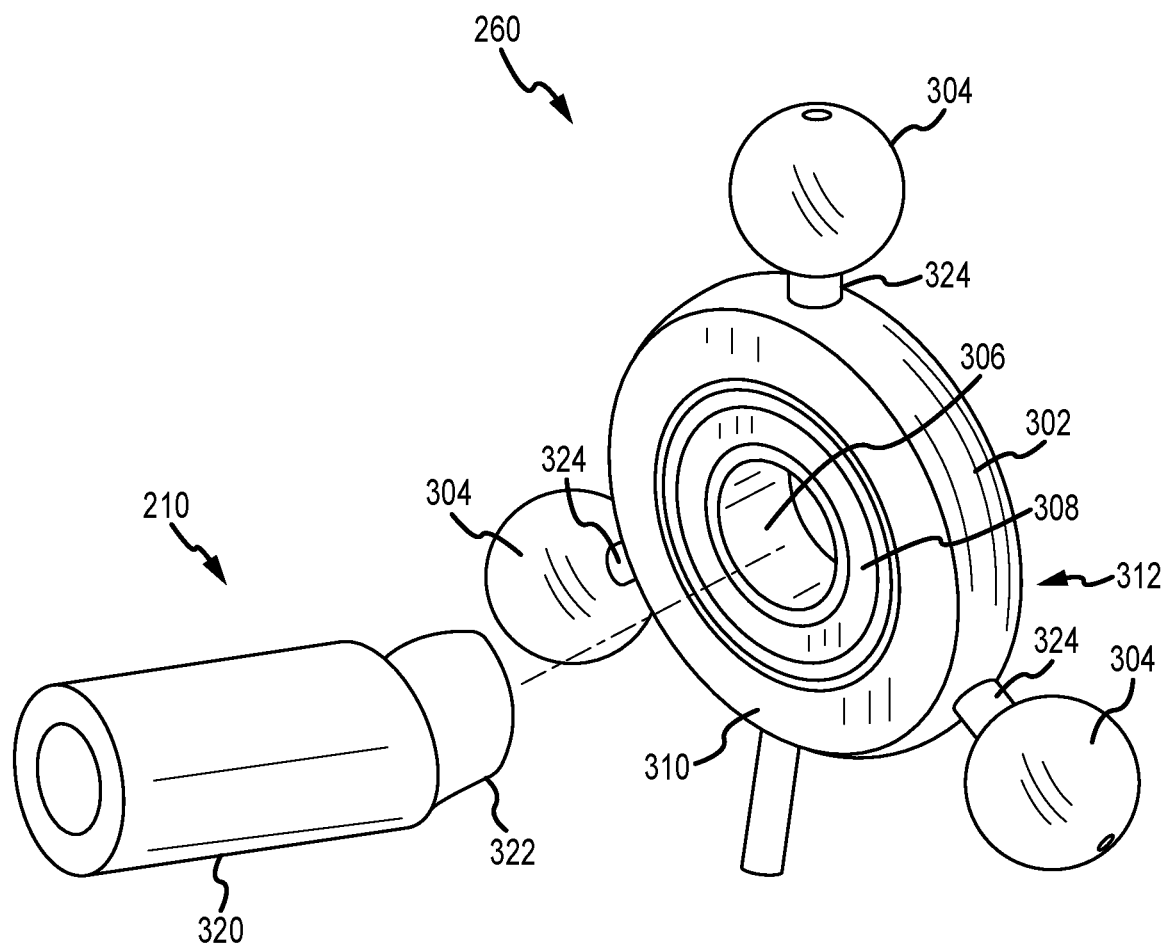
FIG. 6 is a schematic perspective view of the wobble plate assembly, from which the drive shaft is decoupled.

With reference to FIGS. 4-6, an example of the wobble plate assembly 260 is described. In particular, FIG. 5 is a schematic side view of the wobble plate assembly 260 that is operatively coupled to an end of the drive shaft 210, and FIG. 6 is a schematic perspective view of the wobble plate assembly 260, from which the drive shaft 210 is decoupled.

As shown in FIG. 4, the wobble plate assembly 260 is disposed such that the center of the wobble plate assembly 260 is generally aligned with the axis of rotation A of the drive shaft A. The wobble plate assembly 260 includes a hub plate 302 (also referred to herein as a wobble plate) and one or more spherical elements 304 (also referred to herein as balls or distal attachment members). The spherical elements 304 are arranged on different distal portion of the hub plate 302. The spherical elements 304 are spaced apart one another around the periphery of the hub plate 302. In some examples, the number of spherical elements 304 is the same as the number of cylinders 250. For example, since the compressor 200 in the illustrated example has three cylinders, three spherical elements 304 are provided to the hub plate 302 so as to correspond to the cylinders 250.

The hub plate 302 has a first end face 310 and an opposite second end face 312. The hub plate 302 includes a first bore 306 defined on the first end face 310 and configured to operatively engage one end of the drive shaft 210. A bearing element 308 is provided to the bore 306 so as to be disposed between the hub plate 302 and the end of the drive shaft 210. In particular, the hub plate 302 mounts the outer race of the bearing element 308 at the first end face 310 which is opposite to a wobble anti-rotation device 400 and the inner race of the bearing element 308 is fitted to the end of the drive shaft 210. The bearing element 308 is mounted to the bore 306 in various manners. In some examples, the outer race of the bearing element 308 is pressed and/or bonded to the bore 306 of the hub plate 302, and the inner race of the bearing element 308 is similarly pressed and/or bonded to the drive shaft 210. The bearing element 308 can be of various types, such as a ball bearing and a thrust bearing.

As illustrated in FIGS. 4 and 6, the drive shaft 210 is provided with a shaft sleeve 320 mounted onto the end of the drive shaft 210. The shaft sleeve 320 includes an eccentric stub shaft 322 that is fixed at an angle to the drive shaft 210 (i.e., relative to the axis of rotation A). As such, the hub plate 302 is attached to the drive shaft 210 via the bearing element 308 at an angle relative to the drive shaft, around an axis different from the axis of rotation A. Further, the hub plate 302 is coupled to the drive shaft 210 (i.e., the axle) such that each spherical element reciprocates generally in an axial path along the axis of the cylinder. In some examples, the spherical elements reciprocate generally along an arc in a plane that includes the axis of rotation A upon rotation of the axle. In some examples, the spherical elements can reciprocate substantially in three-dimensional orbits that can be generally defined along the axis of the cylinders. In some examples, the reciprocating motions of the spherical elements can vary depending on different types of the wobble anti-rotation device 400 (e.g., a CV joint or a simple distal pin). The eccentric stub shaft 322 is pressed into the inner race of the bearing element 308. In some examples, the shaft sleeve 320 (including the eccentric stub shaft 322) is integrally formed with the drive shaft 210.

In some embodiments, the shaft sleeve 320 and the bearing element 308 are arranged such that a center C of the bearing element 308 is located at the intersection of the axis of rotation A of the drive shaft 210 and a longitudinal axis A3 of the eccentric stub shaft 322 of the shaft sleeve 320. This arrangement can ensure the wobble plate assembly 260 to move as desired. In other embodiments, other configurations may be also possible.

The hub plate 302 further includes a second bore 408 defined on the second end face 312 and configured to engage a wobble anti-rotation device 400, as described in more detail with reference to FIG. 10.

With continued reference to FIGS. 4-6, the spherical elements 304 are connected to the hub plate 302 through arms 324 extending between the periphery of the hub plate 302 and the spherical elements 304. In some examples, the spherical elements 304 are drilled to form holes, which are pressed and/or bonded to one end of the arms 324. The other end of the arms 324 are similarly pressed and/or bonded to holes provided on the periphery of the hub plate 302.

In other examples, the spherical elements 304 are connected to the hub plate 302 in other manners. By way of example, the spherical elements 304 can be integrally formed with the hub plate 302.

The spherical elements 304 can be made of various materials. Some examples of the spherical elements 304 are made of bearing grade steel. Other materials are also possible in other examples.

Figure 8:
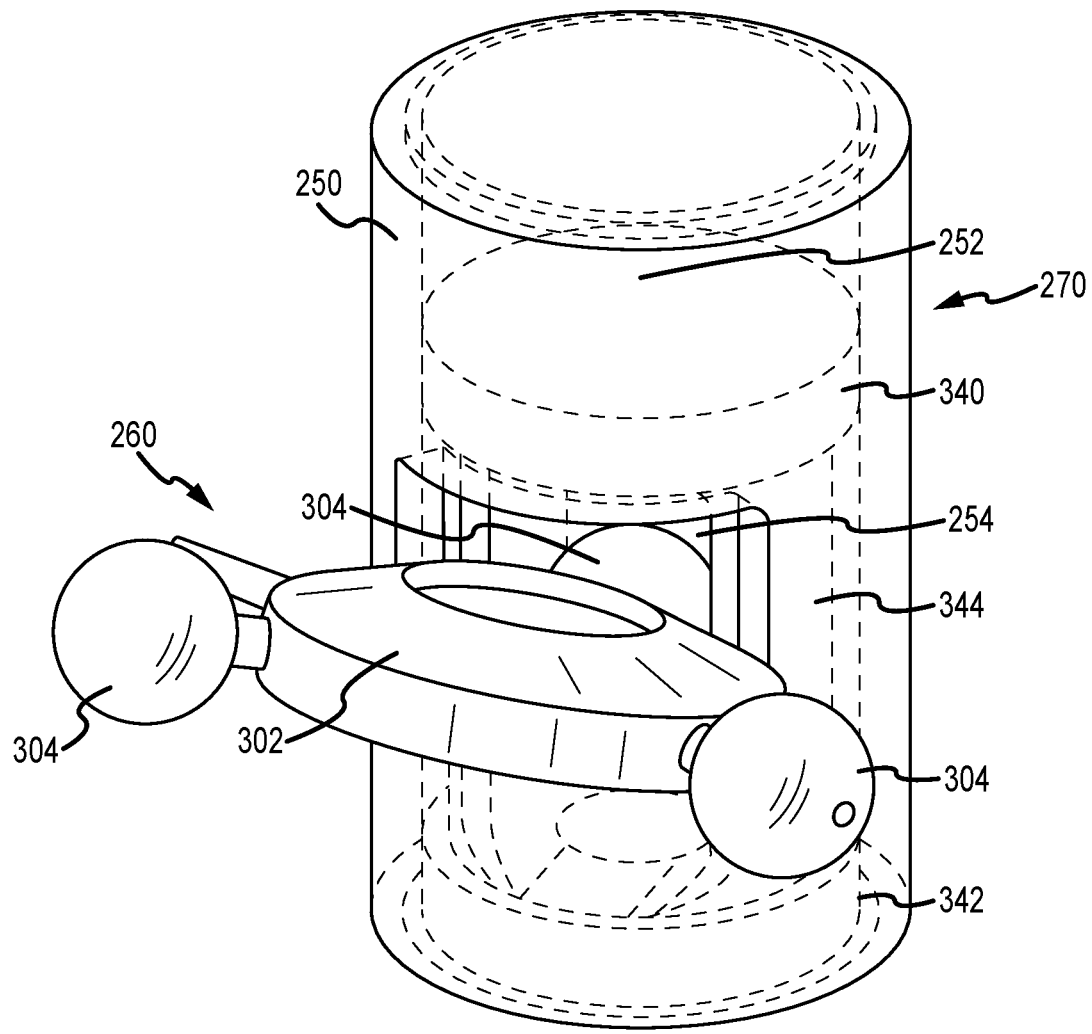
FIG. 8 schematically illustrates the piston assembly within a cylinder.

Referring to FIGS. 4, 7 and 8, an example of the piston assembly 270 is described in more detail. FIG. 7 schematically illustrates the piston assemblies 270 coupled to the wobble plate assembly 260, and FIG. 8 schematically illustrates the piston assembly 270 within the cylinder 250.

Each of the piston assemblies 270 is received within the cylinder 250 and reciprocates therewithin as the wobble plate assembly 260 wobbles. In some examples, the piston assembly 270 reciprocates within its cylinder 250 along a second axis parallel to the axis of rotation A upon rotation of the drive shaft 210. The piston assembly 270 is configured as a double-headed piston that includes a first piston head 340 and a second piston head 342. In the illustrated example, the piston assembly 270 is disposed within the cylinder 250 such that the first piston head 340 faces the first manifold 224 and the second piston head 342 faces the second manifold 226. Accordingly, the piston assembly 270 defines two sub-chambers (also referred to herein as compression chambers), one of which is defined by the cylinder 250, the first piston head 340 and the first manifold 224, and the other which is defined by the cylinder 250, the second piston head 342 and the second manifold 226. Depending on an axial position of the piston assembly 270 within the cylinder 250, the volumes of the sub-chambers change.

As such, in some examples, the cylinder 250 is integrally made as a single piece and defines two compression chambers associated with the opposite piston heads 340 and 342 of the piston assembly 270, respectively. In an embodiment, the unitary cylinder 250 is, essentially, a tube with a window 254 through which the wobble plate assembly 260 engages with the piston assembly 270.

In some examples, the first and second piston heads 340 and 342 are connected via one or more columns 344. The columns 344 can operate to prevent the piston assembly 270 (i.e., the first and second piston heads 340 and 342) from rotating about its axis as the piston assembly 270 reciprocates within the cylinder 250. In other embodiments, the first piston heads 340 and the second piston heads 342 are separately provided.

As also shown in FIG. 7, the piston assembly 270 has axial edges 345 defined by the columns 344. The axial edges 345 are configured to contact a peripheral portion 346 of the hub plate 302 at a low velocity point relative to each other. The contact between the peripheral portion 346 of the hub plate 302 and the axial edges 345 of the piston assembly 270 provides an anti-rotation mechanism for the piston assembly 270 by controlling the rotation of the piston assembly 270 with the cylinder 250 (such as rotations of the piston rods). In some examples, as the wobble plate assembly 260 is operated, the piston assembly 270 is rotatable along its axis of rotation (i.e., the longitudinal axis of the piston) within the cylinder 250 until the hub plate 302 (e.g., the peripheral portion 346 thereof) contacts the axial edges 345 of the columns 344. The peripheral portion 346 of the hub plate 302 has a curvature configured to improve tangency between the mating surfaces of the peripheral portion 346 and the axial edges 345. In some examples, the origin of the curvature is arranged to be coincident with the axis of the drive shaft in order to reduce friction, wear and torque. In some examples, a wear resistant material is provided to either the axial edges 345 and the peripheral portion 346, or both, to reduce friction and wear.

The peripheral portion 346 of the hub plate 302 that is to contact the axial edges 345 can have different shapes. For example, as shown in FIG. 10, the peripheral portion 346 of the hub plate 302 includes flanges 347 formed adjacent to the spherical elements 304. Other configurations are also possible in other examples.

An outer diameter of the piston assembly 270, which may contact with the inner surface of the cylinder 250, is coated with one or more layers of wear resistant and low friction materials. In alternative embodiment, a lip seal may be used here instead or in addition to a wear resistant and low friction coating. In other embodiments, at least a portion of the piston assembly 270 may be made from low-friction material. For example, the first and second piston heads 340 and 342, which may contact with the inner surface of the cylinder 250, are made from low-friction material. For example, the outer diameter of the piston head can be coated with a fluoropolymer-based coating material. One example of the fluoropolymer material is available from Whitford, such as Xylan 1000 series or Xylan 8100 series. Alternatively or in addition, other materials can also be used to make the piston head or coat at least a portion of the piston head. Other examples of such low-friction material can include polyimides and other low friction materials. In yet other examples, at least part of the piston assembly, such as the piston head, can be formed of a material that incorporates dry lubricant, such as a polyimide compounded with graphite. Examples of such a compound include Vespel materials, such as Vespel SP-22, manufactured by DuPont (Delaware, U.S.A.). In one example, the piston head is made of a material that incorporates a polyimide with 40% graphite. In other examples, other amounts of graphite or other types of fillers can be used for polyimide compound.

Such wear resistant and low friction coating can also be used to reduce wear in other locations in the compressor 200. For example, a layer of coating is applied to the peripheral portion 346 of the hub plate 302 that can interface with the axial edges 345 of the columns 344 of the piston assembly 270 as the wobble plate assembly 260 wobbles. In addition or alternatively, the coating can be applied to the corresponding portion (e.g., the axial edges 345) of the columns 344.

The piston assembly 270 further includes a first connecting rod 350 and a second connecting rod 352. The first connecting rod 350 extends between the first piston head 340 and the spherical element 304 of the wobble plate assembly 260 that extends into the piston assembly 270, and the second connecting rod 352 extends between the second piston head 342 and the spherical element 304. As described above, the spherical element 304 is arranged around the hub plate 302 and extends toward the first and second connecting rods 350 and 352 through a window 254 of the cylinder 250.

Figure 15:
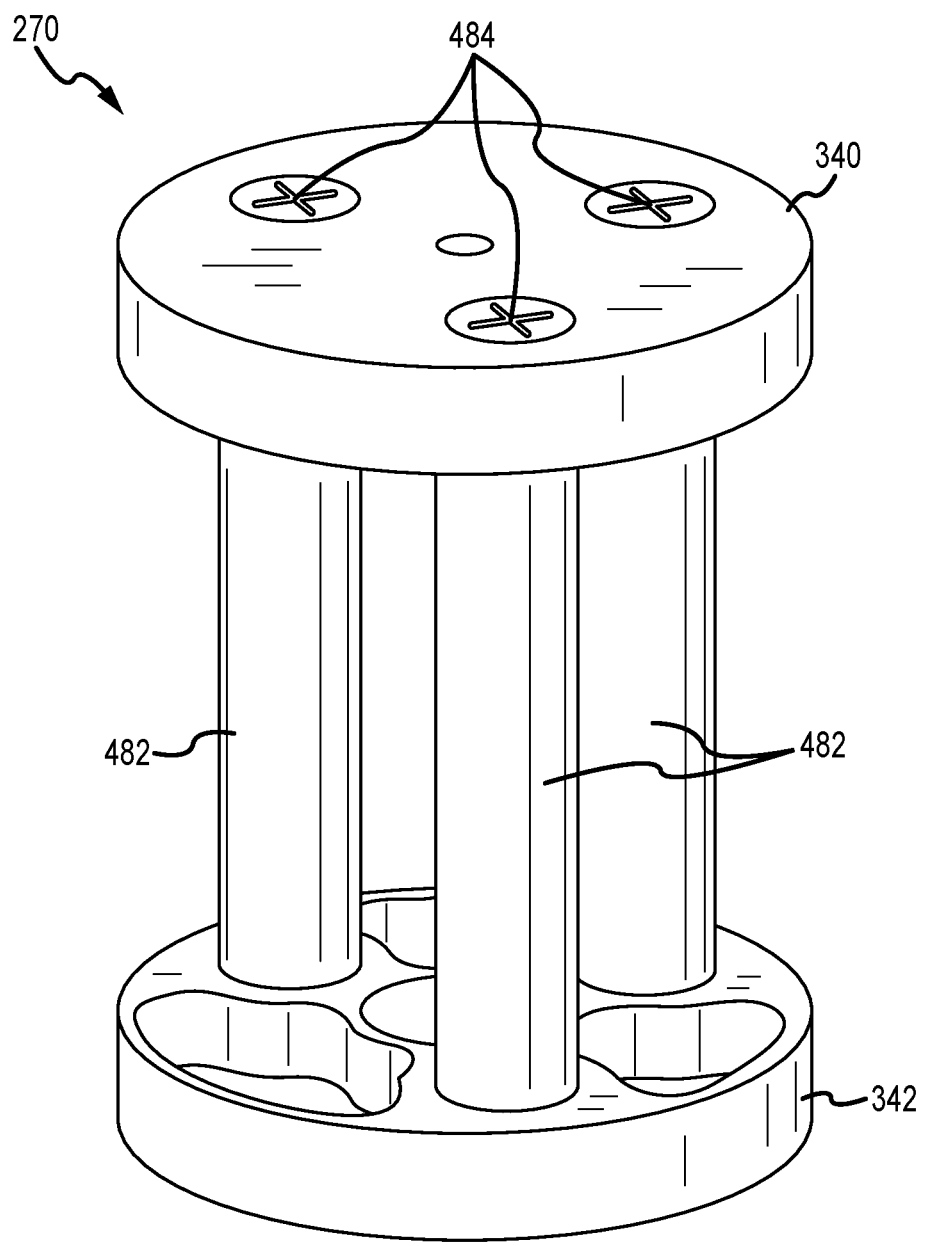
FIG. 15 schematically illustrates another example of the piston assembly.

Another example of the piston assembly 270 is illustrated in FIG. 15. In FIG. 15, the piston assembly 270 is assembled by coupling the first piston head 340 and the second piston head 342 using one or more posts 482. In some examples, the ends of the posts 482 are attached to the first and second piston heads 340 and 342. In the illustrated example, three posts 482 are provided. In other examples, however, other number of posts 482 can be used to make the piston assembly 270. In some embodiments, fasteners 484 (e.g., screws) can be used to attach the posts 482 to the first and second piston heads 340 and 342. In other embodiments, the posts 482 can be glued to the first and second piston heads 340 and 342. Other methods can also be used to attach the posts 482 to the first and second piston heads 340 and 342.

Figure 19:
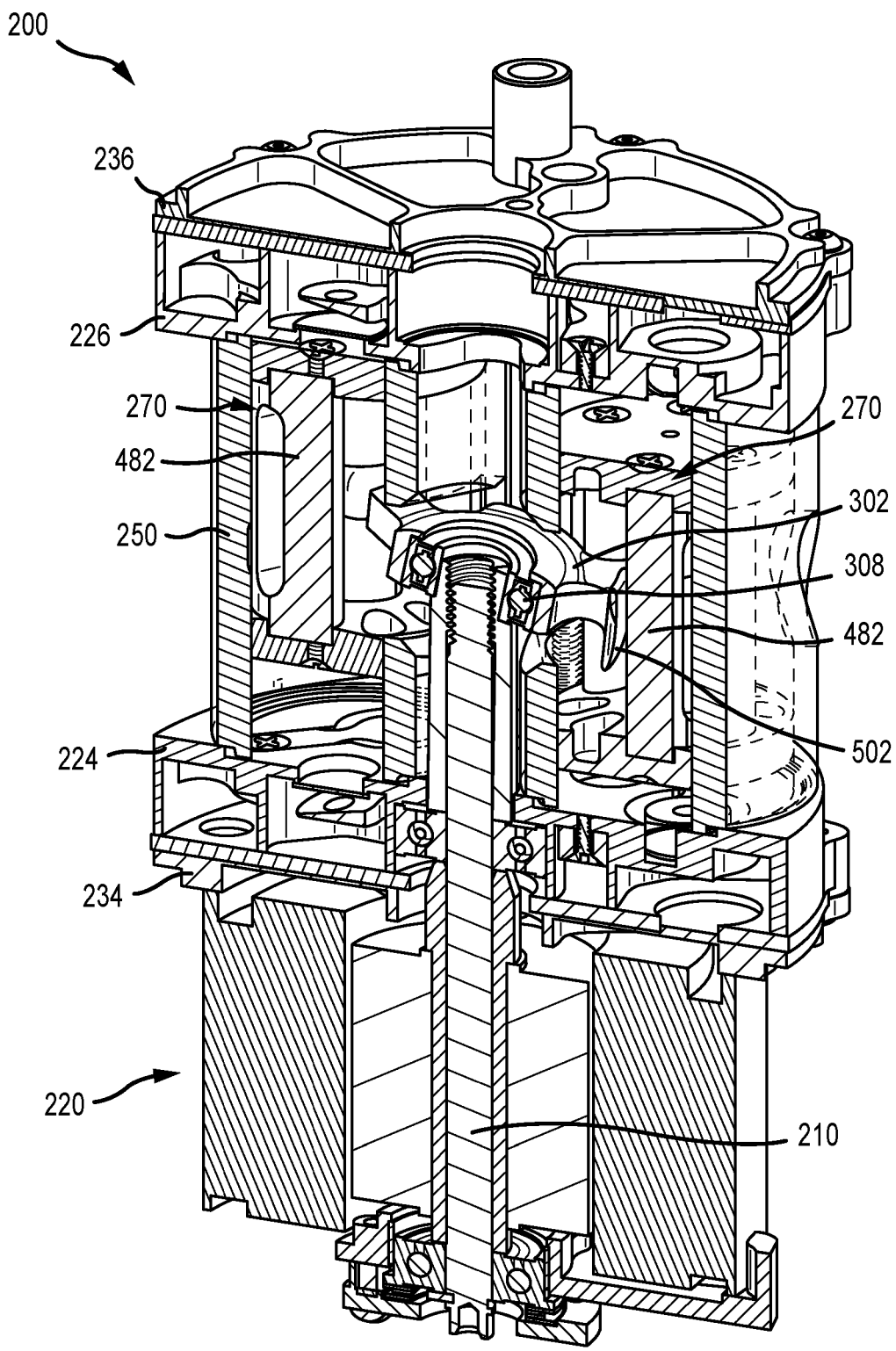
FIG. 19 is a schematic cross sectional view of another exemplary embodiment of the compressor.
Figure 21:
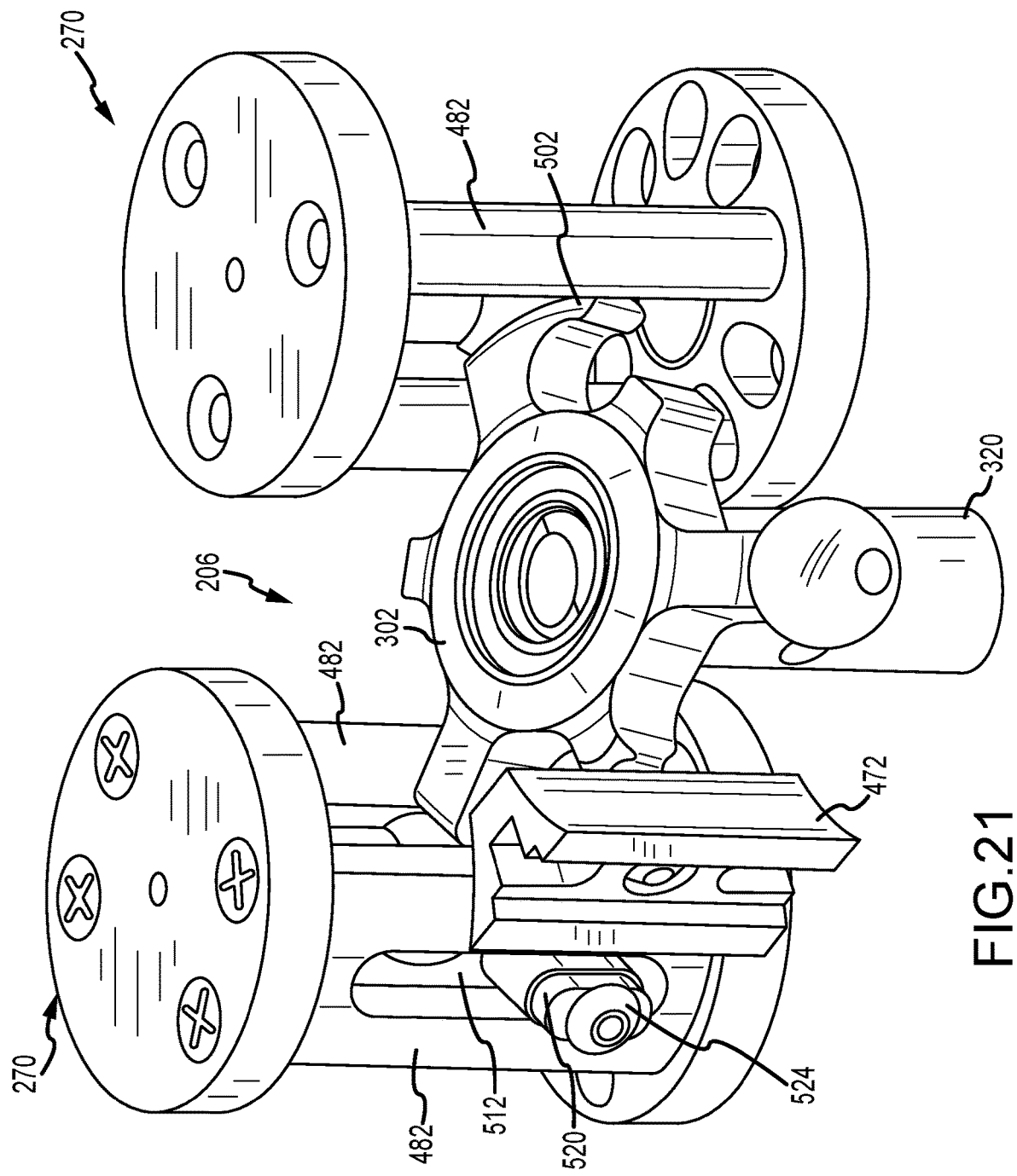
FIG. 21 is a schematic part view of the compressor including the wobble plate assembly and the piston assemblies.
Figure 22:
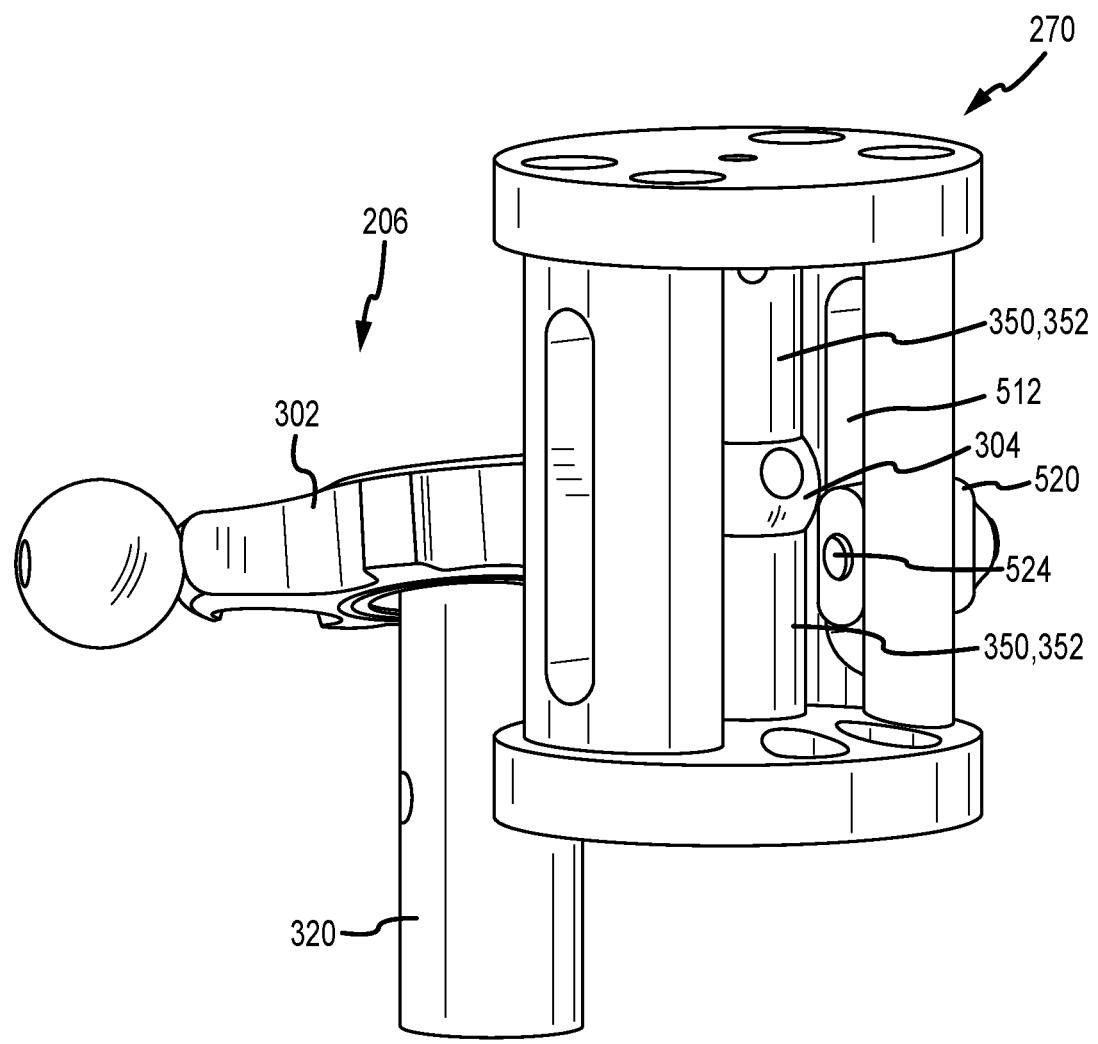
FIG. 22 is another schematic part view of the compressor including the wobble plate assembly and the piston assemblies.
Figure 23:
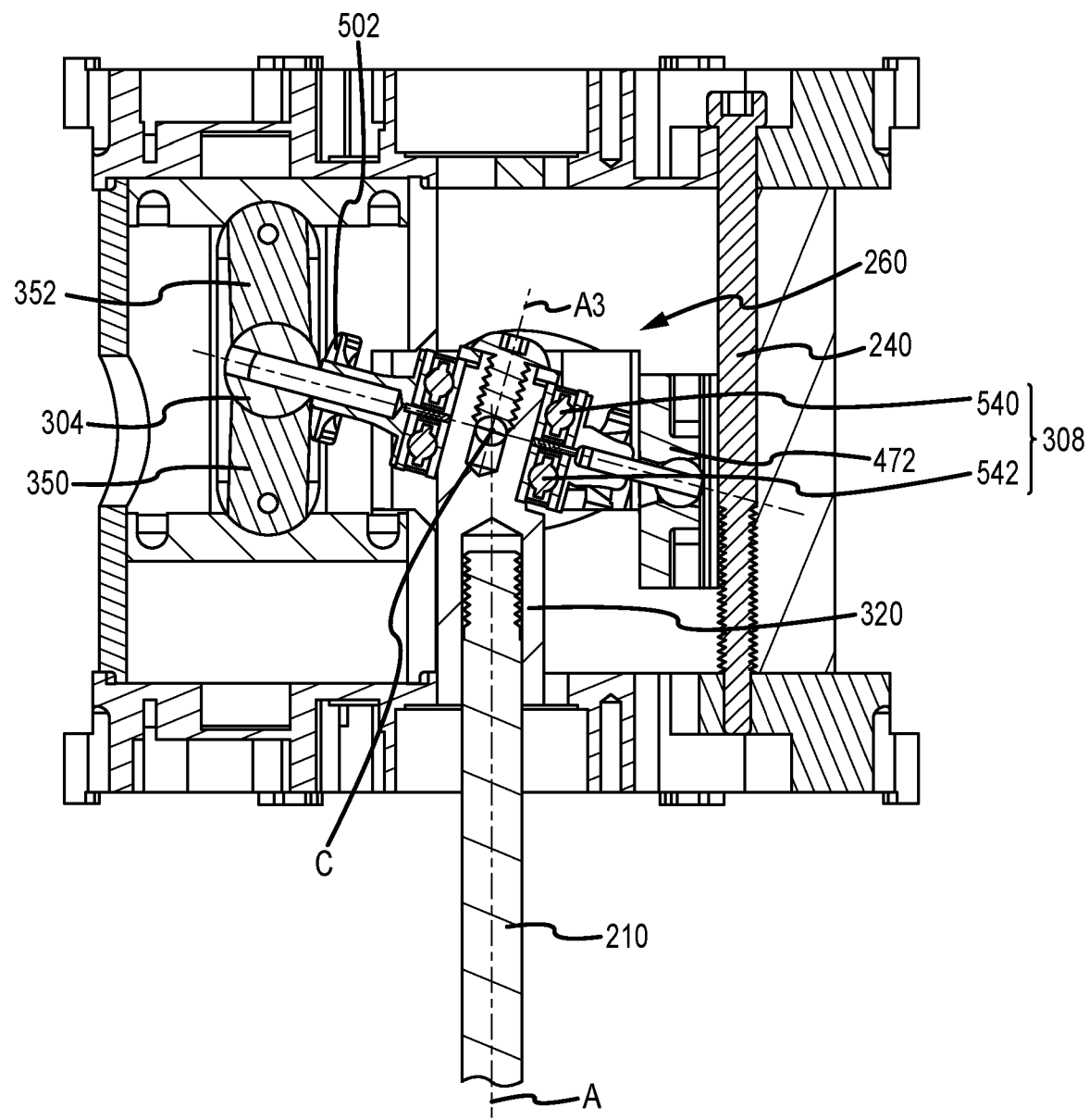
FIG. 23 schematically illustrates another example bearing element included in the wobble plate assembly.
Figure 24:
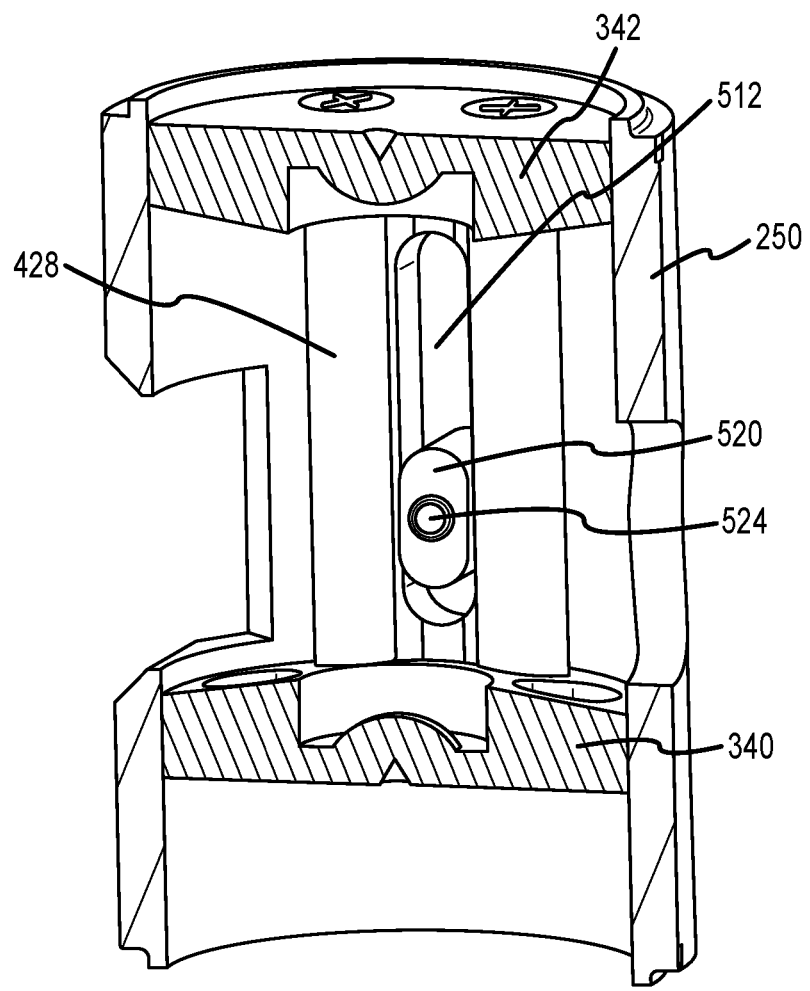
FIG. 24 is a schematic part view of the compressor.
Figure 25:
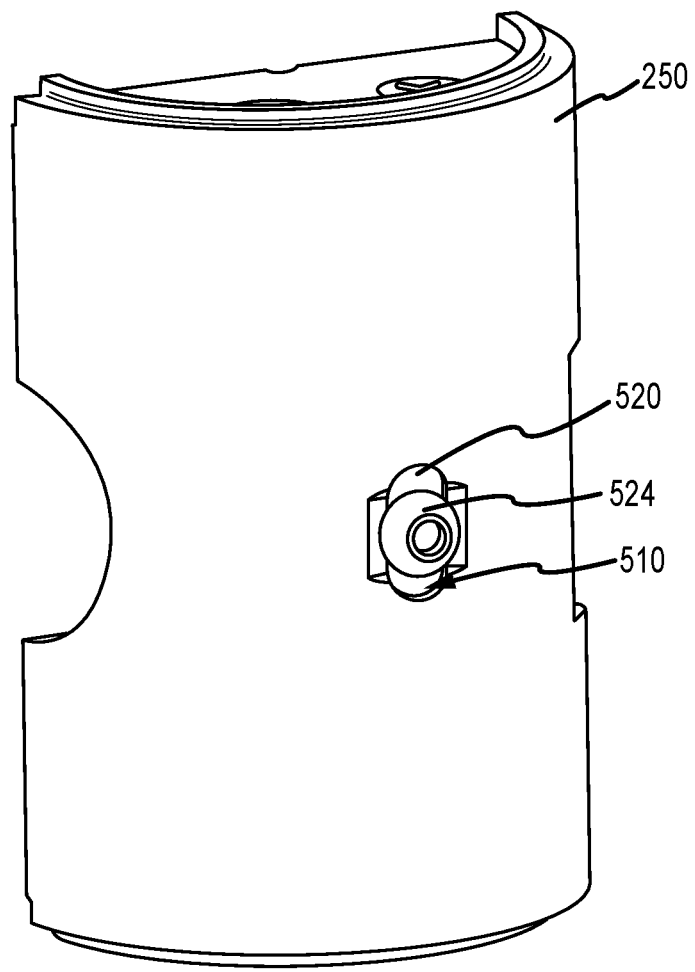
FIG. 25 is another schematic part view of the compressor of FIG. 24.

In some embodiments, the posts 482 of the piston assembly 270 can be used for a piston anti-rotation mechanism for the piston assembly 270. For example, as best shown in FIGS. 19 and 21, the hub plate 302 includes one or more flanges 502 configured to contact at least one of the posts 482 as the wobble plate assembly 260 moves. The peripheral surface of the flange 502 can slide against the associated post 482 as the wobble plate assembly 260 wobbles and thus prevent the piston assembly from rotating about its own axis. The peripheral surface of the flange 502 is configured to provide a curved shape suitable for optimal contact and sliding against the post 482. In some embodiments, the peripheral surface of the flange 502 is formed to be spherical about the center (such as the center C of the bearing element 308 in FIG. 4 or the center C of two bearings 540 and 542 in FIG. 23).

Various configurations of the posts 482 are possible. In the example of FIG. 15, the posts 482 are configured as cylindrical shapes. Other shapes of the posts 482 are illustrated in other figures, such as FIG. 7 (e.g., the column 344) and FIG. 20.

Figure 9:
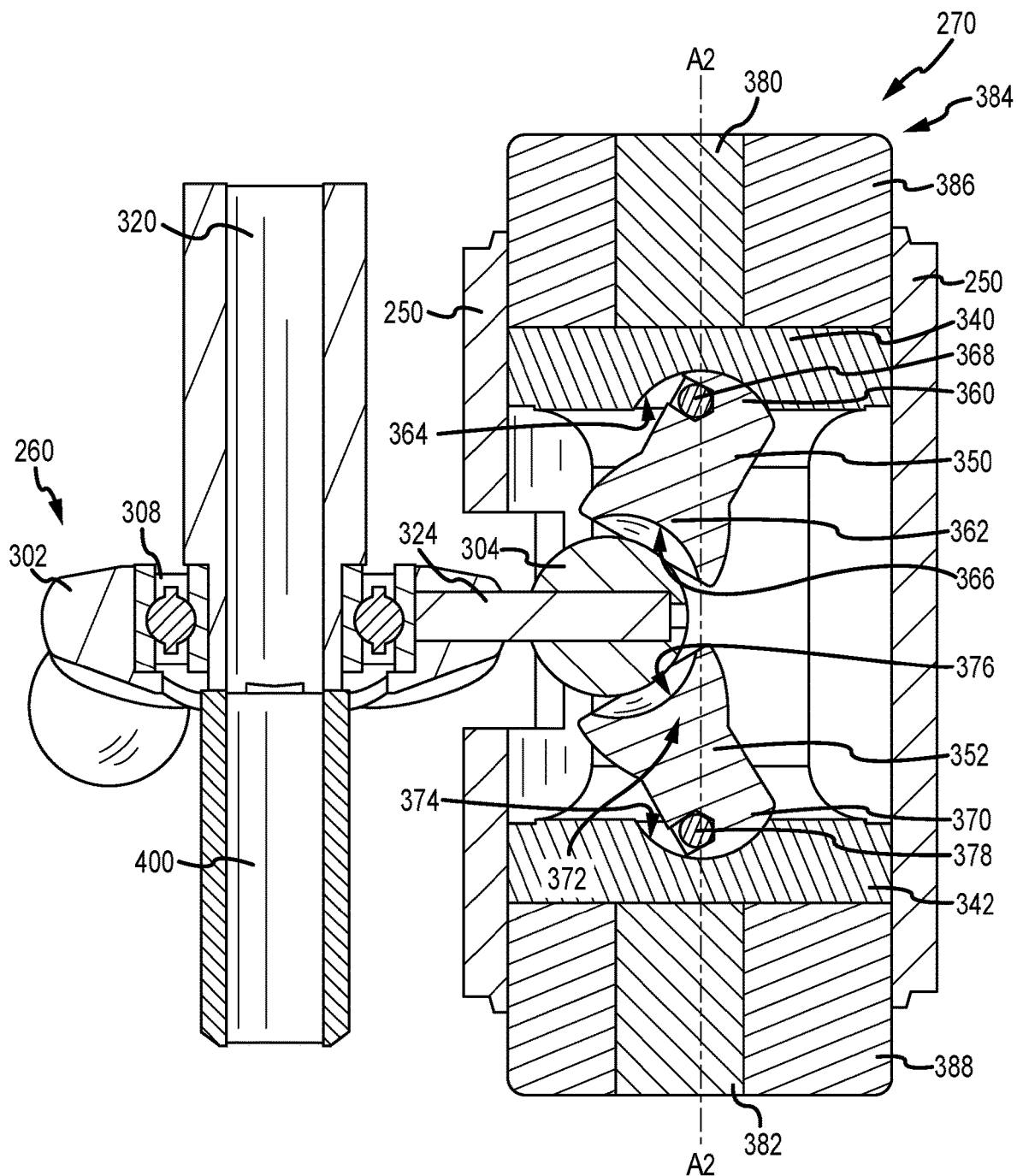
FIG. 9 schematically illustrates coupling of first and second piston heads, first and second connecting rods, and a spherical element.

FIG. 9 schematically illustrates coupling of the first and second piston heads 340 and 342, the first and second connecting rods 350 and 352, and the spherical element 304. This configuration is also illustrated in FIG. 13. As shown in FIGS. 9 and 13, the first connecting rod 350 has a head side end 360 and a distal end 362. The head side end 360 of the first connecting rod 350 spherically mates the first piston head 340, and the distal end 362 of the first connecting rod 350 spherically mates the spherical element 304 of the wobble plate assembly 260. In the illustrated example, the first piston head 340 provides a socket 364 on which the head side end 360 of the first connecting rod 350 slidably seats, and the distal end 362 of the first connecting rod 350 defines a socket 366 on which the spherical element 304 of the wobble plate assembly 260 slidably seats.

The interfaces between the first piston head 340, the first connecting rod 350, and the spherical element 304 can be provided with dry lubricants. In some embodiments, at least one of the first piston head 340, the first connecting rod 350, and the spherical element 304 is formed of a material that incorporates a polyimide compounded with graphite. Examples of such a compound include Vespel materials, such as Vespel SP-22, manufactured by DuPont (Delaware, U.S.A.). In one example, the first connecting rod 350 and the spherical element 304 are made of a material that incorporates a polyimide with 40% graphite. In other examples, other amounts of graphite or other types of fillers can be used for polyimide compound.

In yet other embodiments, the interfaces between the first piston head 340, the first connecting rod 350, and the spherical element 304 can be coated with a layer of wear resistant and low friction materials, such as a fluoropolymer-based coating material. One example of the fluoropolymer material is available from Xylan Coatings, such as Xylan 1000 series or Xylan 8100 series. Other materials can also be used for such coating.

Similarly, the second connecting rod 352 has a head side end 370 and a distal end 372. The head side end 370 of the second connecting rod 352 spherically mates the second piston head 342, and the distal end 372 of the second connecting rod 352 spherically mates the spherical element 304 of the wobble plate assembly 260. In the illustrated example, the second piston head 342 provides a socket 364 on which the head side end 370 of the second connecting rod 352 slidably seats, and the distal end 372 of the second connecting rod 352 defines a socket 376 on which the spherical element 304 of the wobble plate assembly 260 slidably seats. The interfaces between the second piston head 342, the second connecting rod 352, and the spherical element 304 can be provided with dry lubricants in the same or similar manners as the interfaces between the first piston head 340, the first connecting rod 350, and the spherical element 304, as described above.

Figure 26:
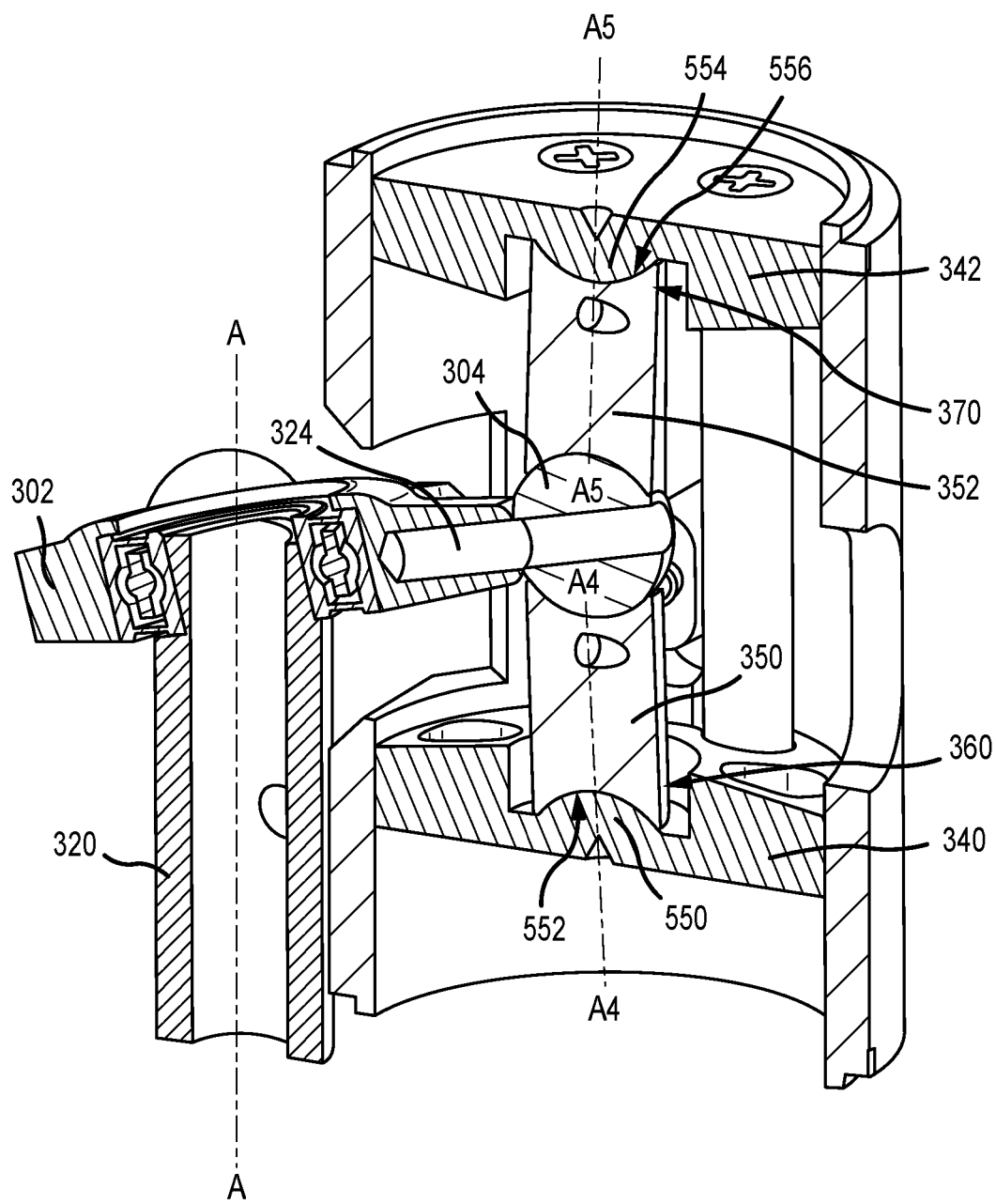
FIG. 26 schematically illustrates another example of the piston assembly.

In other embodiments, the interface between the piston head 340, 342 and the head side ends 360, 370 of the connecting rods 350, 352 can have different configurations. For example, as illustrated in FIG. 26, the first piston head 340 provides a convex portion 550, and the head side end 360 of the first connecting rod 350 is configured to form a socket 552 (or a concave portion) that correspond to the convex portion 550 of the first piston head 340. The socket 552 of the first connecting rod 350 at the head side end 360 can slidably seat on the convex portion 550 of the first piston head 340 so that the head side end 360 of the first connecting rod 350 spherically mates the first piston head 340.

Similarly, as illustrated in FIG. 26, the second piston head 342 provides a convex portion 554, and the head side end 370 of the second connecting rod 352 is configured to form a socket 556 (or a concave portion) that correspond to the convex portion 554 of the second piston head 342. The socket 556 of the second connecting rod 352 at the head side end 370 can slidably seat on the convex portion 554 of the second piston head 342 so that the head side end 370 of the second connecting rod 352 spherically mates the second piston head 342.

The configuration as illustrated in FIG. 26 can effectively increase the length of the connecting rods 350, 352, thereby decreasing the sidewise movements of the connecting rods 350, 352 as the wobble plate assembly 260 wobbles. For example, as the effective length of the first connecting rod 350 increases, the angle between an axis A4 of the first connecting rod 350 and the axis A of the drive shaft can decrease. Similarly, the effective length of the second connecting rod 352 increases, the angle between an axis A5 of the second connecting rod 352 and the axis A of the drive shaft can decrease. A smaller angle of the connecting rods 350, 352 relative to the axis A of the drive shaft can reduce the sidewise movement of the connecting rods 350, 352.

In other embodiments, the spherical element 304 and the sockets 366 and 376 can have different configurations to the extent that the spherical elements 304 can slidably engage with the sockets 366 and 376. For example, the curved interfaces between the spherical element 304 and each of the sockets 366 and 376 can be reversed.

Although it is primarily illustrated in this document that the distal attachment members 304 are described as the spherical elements, the distal attachment members 304 have different shapes in other embodiments. Accordingly, the distal ends 362 and 372 of the first and second connecting rods 350 and 352 may have different shapes that are complementary with the shape of an associated distal attachment member 304. For example, the distal ends 362 and 372 of the first and second connecting rods 350 and 352 can have convex surfaces (i.e., outwardly curved surfaces) while the associated distal attachment member 304 includes concave surfaces (i.e., inwardly curved surfaces) that corresponds to the convex surfaces of the first and second connecting rods 350 and 352. In some embodiments, the distal ends 362 and 372 of the first and second connecting rods 350 and 352 can have identical end surfaces. In other embodiments, the distal ends 362 and 372 of the first and second connecting rods 350 and 352 have different end surfaces (e.g., one of the distal ends 362 and 372 has a concave surface (e.g., a socket) and the other has a convex surface), and the associated distal attachment member 304 has two different surfaces that correspond to the different end surface of the distal ends 362 and 372 of the first and second connecting rods 350 and 352, respectively.

In some examples, an assembly tool 384 is provided to assemble the piston assembly 270 with the wobble plate assembly 260. The assembly tool 384 is used to temporarily adjust the first connecting rod 350 and the second connection rod 352 at a particular arrangement. For example, the assembly tool 384 is configured to interact with the first and second connecting rods 350 and 352 and arrange at a particular position with respect to the first piston head 340 and the second piston head 342, respectively (and thereby with respect to the spherical element 304 of the hub assembly). The assembly tool 384 can include a first arrangement device 386 and a second arrangement device 388.

The first arrangement device 386 includes a magnetic element 380. Correspondingly, the first connecting rod 350 includes a magnetic element 368, which may be embedded therein at the head side end 360. For example, the magnetic element 380 includes a magnet, and the magnetic element 368 includes a ferromagnetic material. The magnetic element 368 can be shaped as a ball and contained in the head side end 360. The magnetic element 380 included in the first arrangement device 386 is configured to magnetically attract the magnetic element 368 of the first connecting rod 350 when the first arrangement device 386 is disposed adjacent the first piston head 340. In some examples, during assembly, the first arrangement device 386 is arranged above the first piston head 340 as shown in FIG. 9 so that the magnetic element 368 and the magnetic element 380 are relatively arranged. In this arrangement, the magnetic attraction between the magnetic element 368 and the magnetic element 380 biases the distal end 362 of the first connecting rod 350 toward the window 254 of the cylinder 250 so that the first connecting rod 350 is easily accessible for mating the spherical element 304 with the distal end 362 of the first connecting rod 350.

Similarly, the second arrangement device 388 includes a magnetic element 382. Correspondingly, the second connecting rod 352 includes a magnetic element 378, which may be embedded therein at the head side end 370. For example, the magnetic element 382 includes a magnet, and the magnetic element 378 includes a ferromagnetic material. The magnetic element 378 can be shaped as a ball and contained in the head side end 370. The magnetic element 382 included in the second arrangement device 388 is configured to magnetically attract the magnetic element 378 of the second connecting rod 352 when the second arrangement device 388 is disposed adjacent the second piston head 342. In some examples, when the first arrangement device 386 is disposed above the first piston head 340 as described above, the second arrangement device 388 can be similarly arranged above the second piston head 342 as shown in FIG. 9 so that the magnetic element 378 and the magnetic element 382 are relatively arranged. In this arrangement, the magnetic attraction between the magnetic element 378 and the magnetic element 382 biases the distal end 372 of the second connecting rod 352 toward the window 254 of the cylinder 250 so that the second connecting rod 352 is easily accessible for mating the spherical element 304 with the distal end 372 of the second connecting rod 352.

As such, the assembly tool 384 including the first and second arrangement devices 388 is configured and used to temporarily arrange the distal ends of the first and second connecting rods 350 and 352 toward the window 254 of the cylinder 250 together so that the spherical element 304 of the wobble plate assembly 260 is easily and fully coupled with the distal ends (and trapped therebetween) of the first and second connecting rods 350 and 352. Once the mating between the spherical element of the wobble plate assembly and the connecting rods of the piston assembly is complete, the assembly tool 384 can be removed. After the removal of the assembly tool 384, the magnetic elements 368 and 378 have no effect on the operation of the compressor 200.

As the wobble plate assembly 260 is orbitally tilted by rotation of the drive shaft 210, the first connecting rod 350 and the second connecting rod 352 can move slightly off a longitudinal axis A2 of the piston assembly 270. Such off-axis motion of the first and second connecting rods 350 and 352 accommodates the non-axial motion of the spherical element 304 within the cylinder 250, thereby reducing the side loads of the piston assembly 270 to the cylinder 250.

In some examples, the first connecting rod 350 and the second connecting rod 352 are made of low friction materials. For example, the first and second connecting rods 350 and 352 are made of a material that incorporates a polyimide compounded with graphite. Examples of such a compound include Vespel materials, such as Vespel SP-22, manufactured by DuPont (Delaware, U.S.A.). In one example, the first and second connecting rods are formed of a material that incorporates a polyimide with 40% graphite. In other examples, other amounts of graphite or other types of fillers can be used for polyimide compound.

In the illustrated example, it is primarily described that the piston assembly 270 includes two connecting rods. In other examples, however, the piston assembly 270 has one connecting rod that operatively connects the piston assembly 270 with the spherical element 304 of the wobble plate assembly 260. In yet other examples, the piston assembly 270 includes three or more connecting rods for connecting the piston assembly 270 with the spherical element 304 of the wobble plate assembly 260.

Referring again to FIG. 7, the cylinders 250 are arranged around the wobble plate assembly 260, and preferably equidistant from the axis of rotation A of the drive shaft 210. When the drive shaft 210 is rotated, the hub plate 302 of the wobble plate assembly 260 is not configured to spin. As shown in FIG. 4, a wobble anti-rotation device 400 is provided in the compressor 200 to prevent rotation of the hub plate 302 (i.e., an anti-rotation mechanism for the wobble plate assembly). As such, the bearing element 308 and the wobble anti-rotation device 400 cooperate to prevent the hub plate 302 from spinning about the axis of rotation A as the drive shaft 210 rotates. The hub plate 302 of the wobble plate assembly 260 wobbles (e.g., orbitally tilts) as dictated by an angle of the eccentric stub shaft 322 of the shaft sleeve 320.

Figure 10:
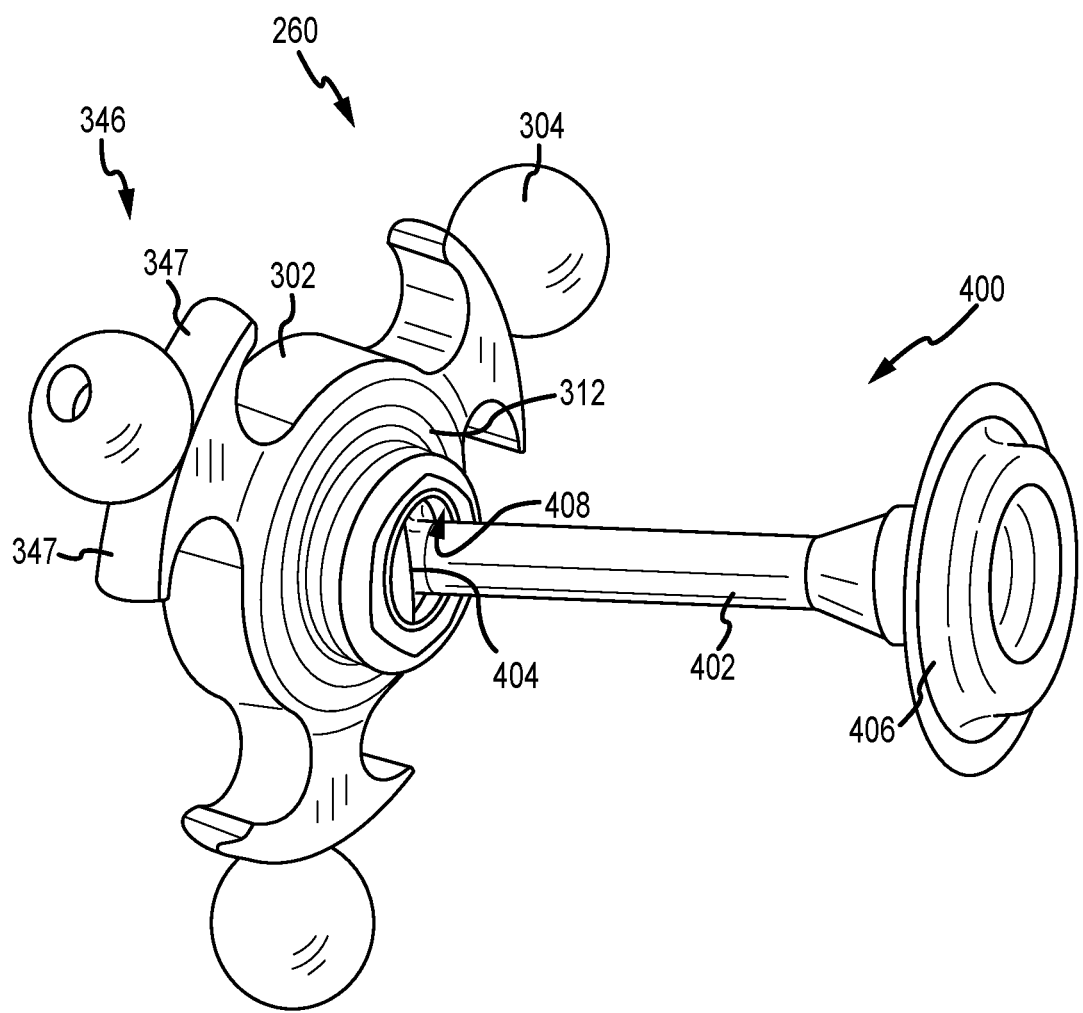
FIG. 10 schematically illustrates an example wobble anti-rotation device coupled to the wobble plate assembly.

FIG. 10 schematically illustrates an example of the wobble anti-rotation device 400 coupled to the wobble plate assembly 260. In the illustrated example, the wobble anti-rotation device 400 is configured as a constant velocity (CV) joint, including a joint shaft 402. A first end 404 of the joint shaft 402 is coupled to the second bore 408 on the second end face 312 of the hub plate 302, and an opposite second end 406 of the joint shaft 402 is flexibly attached to a fixed portion of the housing 202, such as the second manifold 226 and/or the second cover 236.

As the drive shaft 210 rotates, the wobble anti-rotation device 400 permits the shaft sleeve 320 (including the eccentric stub shaft 322) to impart a wobbling motion to the hub plate 302. Where three cylinders 250, three piston assemblies 270, and three spherical elements 304 are provided, the piston assemblies 270 can be arranged 120 degrees apart around the wobble plate assembly 260, and therefore reciprocate within their respective cylinders 120 degree out of phase with one another. Other arrangements of the piston assemblies can also possible in other embodiments.

The wobble anti-rotation device 400, such as a CV joint, prevents the drag torque that the pistons would otherwise bear with flank loads on the cylinders. As such, the wobble anti-rotation device 400 can eliminate the friction at the pistons and thereby improve life expectancy of piston and cylinders.

Figure 16:
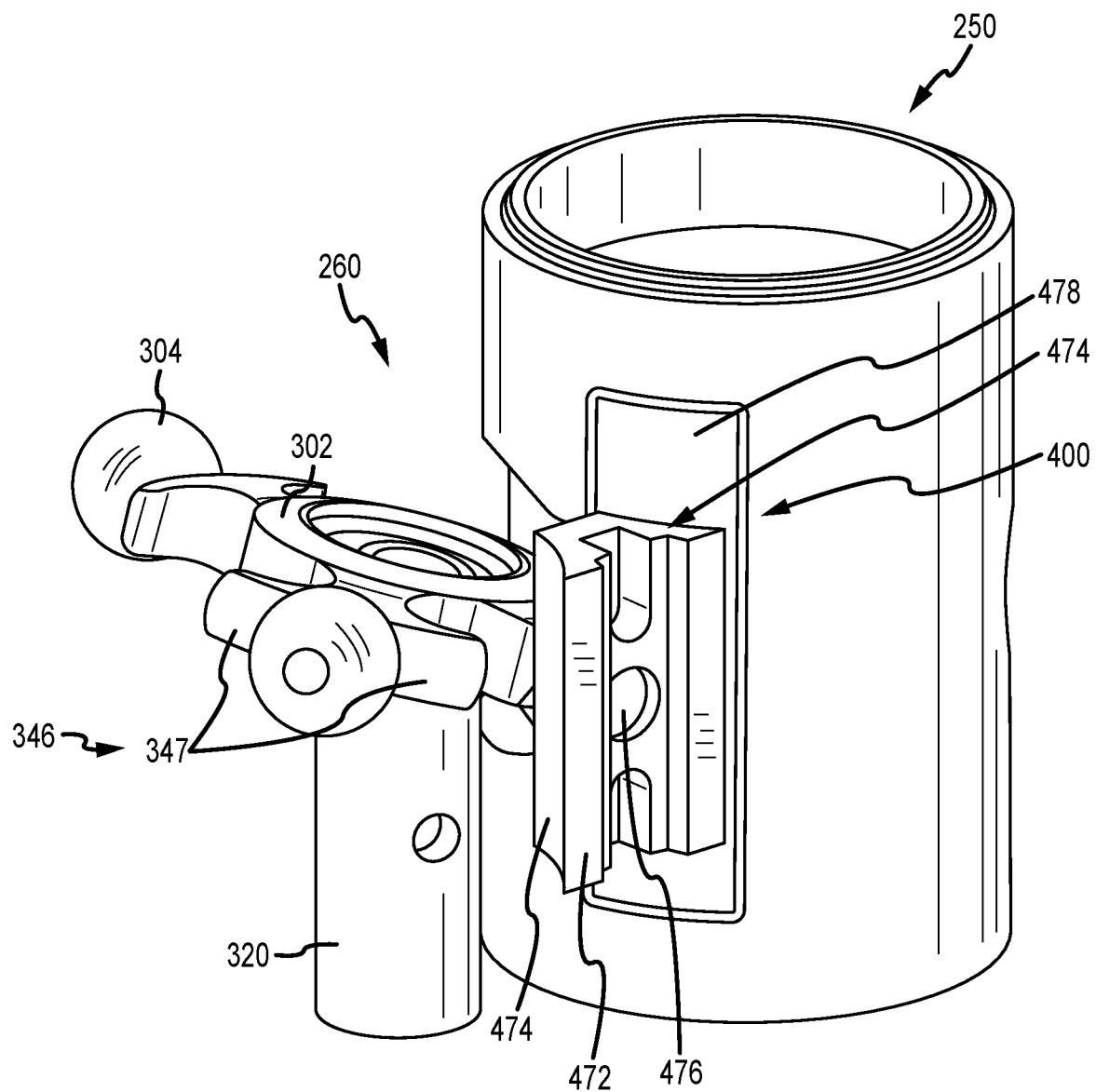
FIG. 16 schematically illustrates another example wobble anti-rotation device coupled to the wobble plate assembly.
Figure 17:
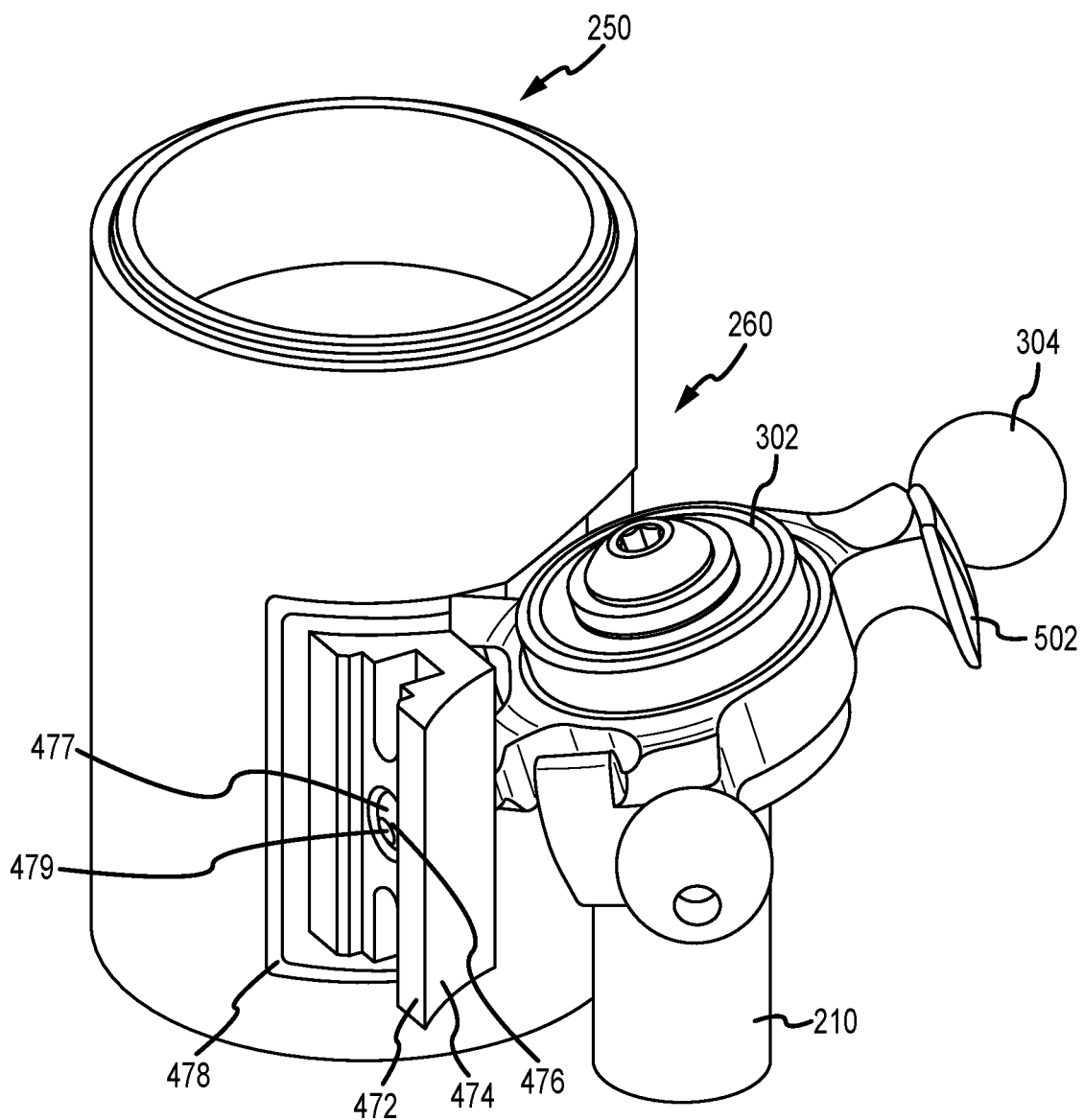
FIG. 17 schematically illustrates yet another example wobble anti-rotation device coupled to the wobble plate assembly.
Figure 18:
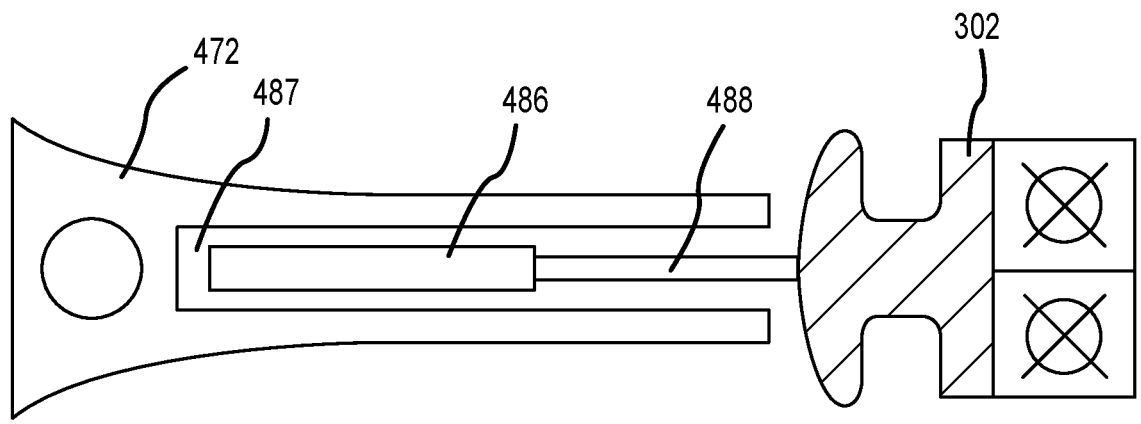
FIG. 18 schematically illustrates yet another example wobble anti-rotation device coupled to the wobble plate assembly.
Figure 18:
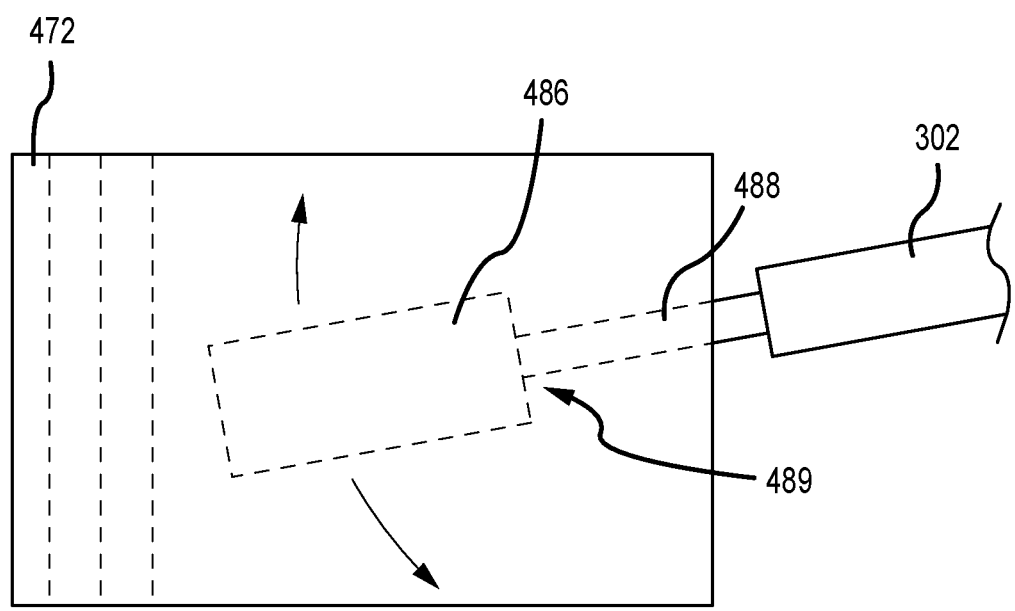

In other examples, other types of the wobble anti-rotation device 400 can be used, such as a universal joint, a simple pin engaging a wear surface, or other devices suitable to prevent or reduce rotation of the hub plate 302. One example of such a wobble anti-rotation device 400 is illustrated in FIGS. 16 and 17. Another example of the wobble anti-rotation device 400 is illustrated in FIG. 18.

Figure 20:
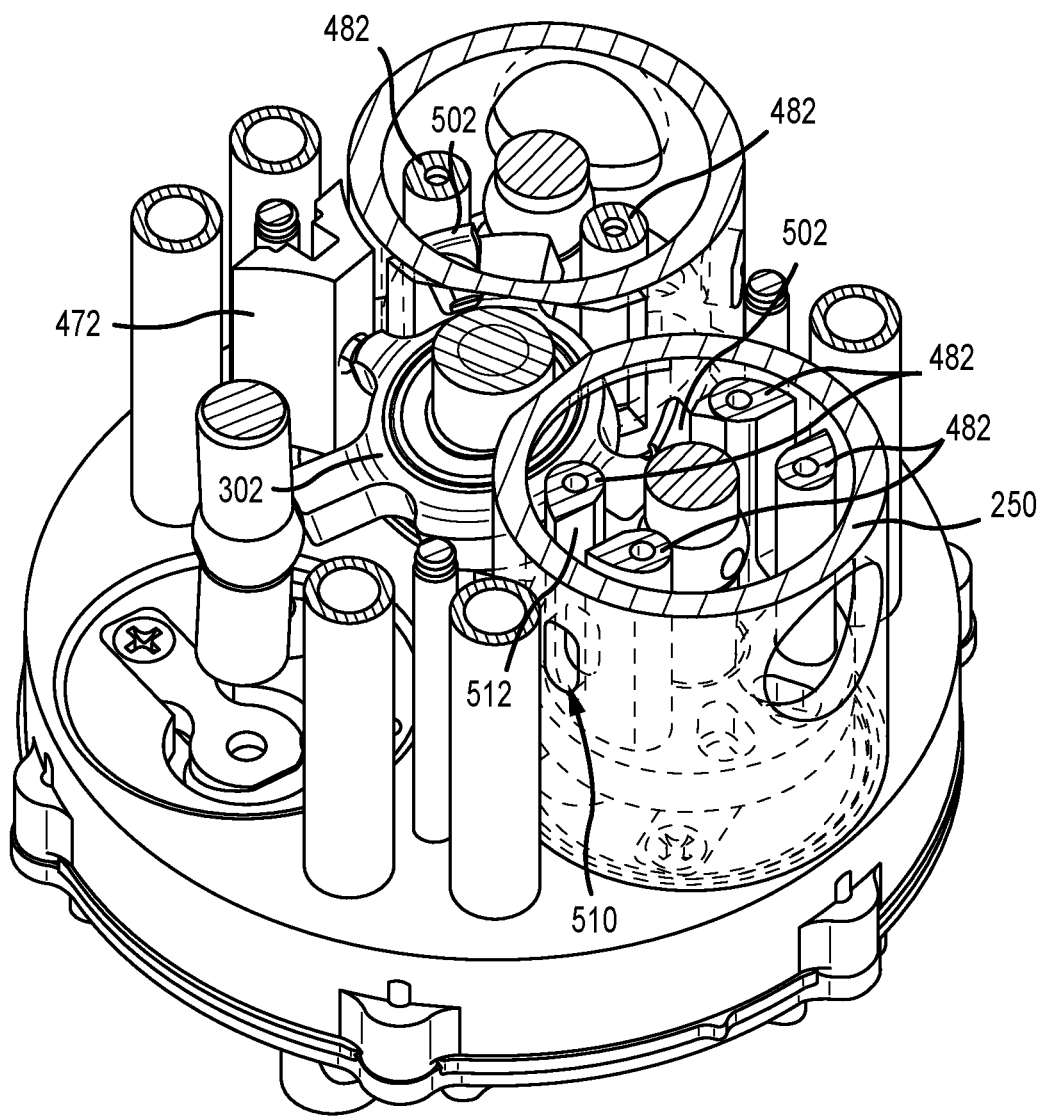
FIG. 20 is a schematic part view of the compressor.

In FIGS. 16, 17, and 20, the wobble anti-rotation device 400 includes a shoe 472 configured to contact and slide against the exterior of the cylinder 250. In some examples, the shoe 472 is generally shaped to be rectangular and extends along the axis of the cylinder 250. The shoe 472 provides a cylinder contact surface 474 configured to contact an exterior surface of the cylinder 250 while the shoe 472 axially moves along the cylinder 250. In some examples, the cylinder contact surface 474 provides a curved surface that corresponds to the curvature of the exterior surface of the cylinder 250 against the shoe 472 slides. The shoe 472 can have two opposite cylinder contact surfaces 474 that contact the exterior surfaces of adjacent cylinders 250, respectively. The shoe 472 can be pivotally coupled to the wobble plate assembly 260. In some examples, a shoe spherical element 476 is provided to pivotally couple the shoe 472 to the hub plate 302 of the wobble plate assembly 260. In some embodiments, a pin (not shown) extends from the hub plate 302 and is fixed into a hole 479 of the shoe spherical element 476. The shoe spherical element 476 is pivotally received in a cavity 477 of the shoe 472 such that the shoe 472 pivots on the shoe spherical element 476.

The shoe 472 can be made of a material that incorporates dry lubricant. In some embodiments, the shoe 472 is made of a polymer material compounded with at least one of graphite, PTFE (Polytetrafluoroethylene), bronze, and other materials. The polymer material can be polyimide (PI), Polyetheretherketone (PEEK), or other thermoplastic materials. One example of such compounded material is one of the VICTREX PEEK polymers, such as 450FC30. In other embodiments, the shoe 472 can be made of a material that incorporates a polyimide compounded with graphite. Examples of such a compound include Vespel materials, such as Vespel SP-22, manufactured by DuPont (Delaware, U.S.A.). In addition or alternatively, the shoe 472 can be coated with a layer of wear resistant and low friction materials, such as a fluoropolymer-based coating material. One example of the fluoropolymer material is available from Whitford, such as Xylan 1000 series or Xylan 8100 series. Other materials can also be used for such coating.

In some examples, a sliding surface 478 can be provided to the exterior of the cylinder 250 so that the cylinder contact surface 474 of the shoe 472 slides against the sliding surface 478. In some examples, the sliding surface 478 can be made as a thin pad and attached to the exterior of the cylinder 250. In other examples, the sliding surface 478 is integrally formed on the exterior of the cylinder 250. The sliding surface 478 can be made from low friction material, such as a fluoropolymer-based coating material. One example of the fluoropolymer material is available from Xylan Coatings, such as Xylan 1000 series or Xylan 8100 series. Other materials can also be used for such coating.

In some examples, the sliding surface 478 is recessed from the exterior of the cylinder 250. In other examples, the sliding surface 478 is flush with the exterior of the cylinder 250. In other examples, the sliding surface 478 is raised from the exterior of the cylinder 250.

In the illustrated example, a single shoe 472 is provided to the wobble plate assembly 260. In other examples, however, the assembly 260 can include two or more shoes 472.

In FIG. 18, the wobble anti-rotation device 400 provides a modified structure for connecting the shoe 472 and the hub plate 302. For example, the wobble anti-rotation device 400 of FIG. 18 includes a paddle 486 that replaces the shoe spherical element 476 of FIGS. 16 and 17. The paddle 486 is movably engaged with the shoe 472. In some embodiments, the paddle 486 is displaceable along a longitudinal slot 487 of the shoe 472 (e.g., moves vertically in the side view of FIG. 18) while the paddle 486 is pivotable about a pin 488 (which can be the same pin as discussed with reference to FIGS. 16 and 17) that extends between the paddle 486 and the hub plate 302. The longitudinal slot 487 can be configured to guide the paddle 486 to move therealong to a limited extent. A pivot point 489 can be formed at the interface between the paddle 486 and the pin 488.

Figure 12:
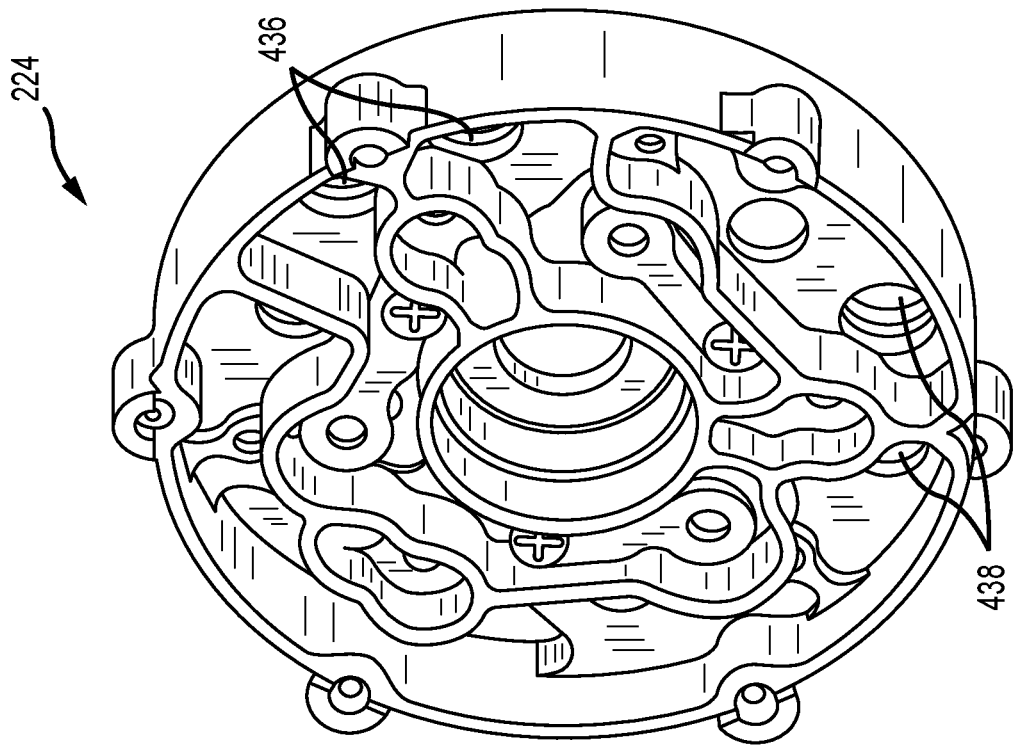
FIG. 12 schematically illustrates an example first manifold.
Figure 11:
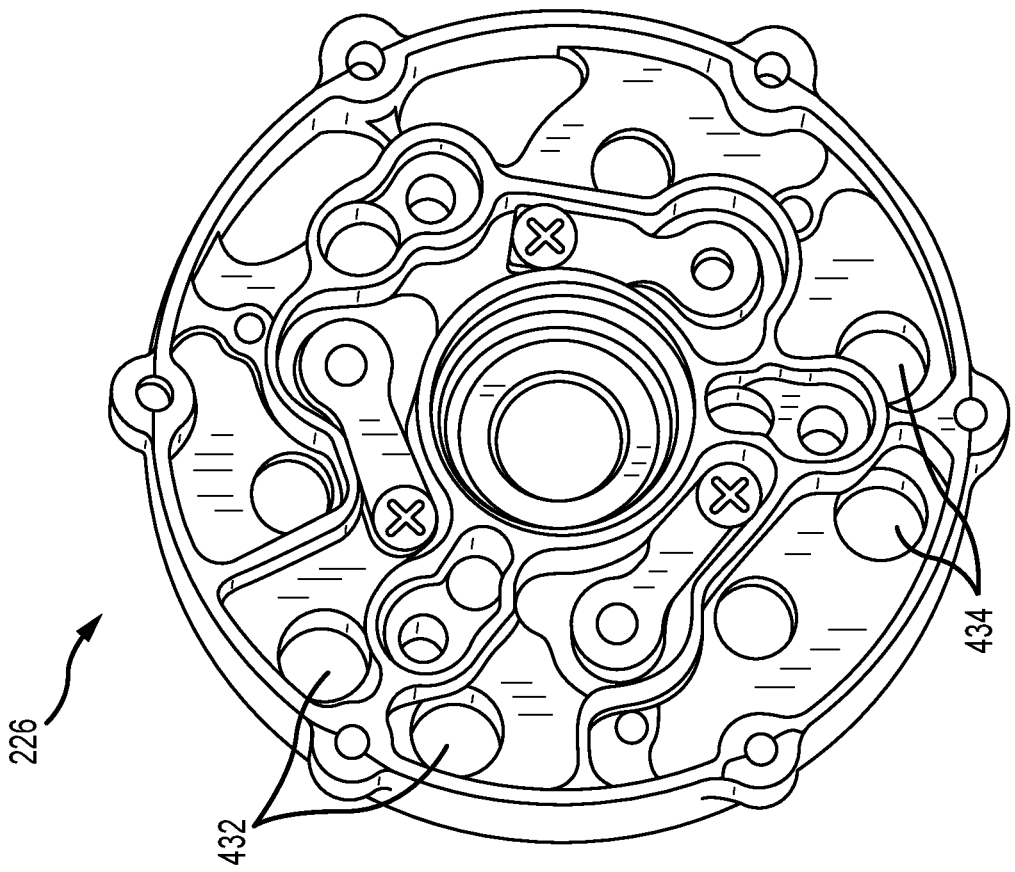
FIG. 11 schematically illustrates an example second manifold.

Referring to FIGS. 11-13, the first manifold 224 and the second manifold 226 are described in more detail. In particular, FIG. 11 schematically illustrates an example of the second manifold 226, and FIG. 12 schematically illustrates an example of the first manifold 224. FIG. 13 schematically illustrates the second manifold 226 connected to the wobble plate assembly 260, which is coupled to the piston assemblies 270 contained within respective cylinders 250.

As described above, the first and second manifolds 224 and 226 are opposingly arranged to capture the cylinders 250 therebetween. In some examples, the first and second manifolds 224 and 226 are symmetrically configured as a mirror of each other so that the opposing cylinder heads perform the same function but 180 degree out of phase.

In some examples, the second manifold 226 includes two suction ports 432 that are provided independently and arranged adjacent each other, and two exhaust ports 434 that are provided independently and arranged adjacent each other. Similarly, the first manifold 224 includes two suction ports 436 that are provided independently and arranged adjacent each other, and two exhaust ports 438 that are provided independently and arranged adjacent each other. The ports 432 and 434 of the second manifold 226 is in fluid communication with the ports 436 and 438 of the first manifold 224, respectively, through four cross-over conduits 440 (FIGS. 3 and 4). In some examples, at least one of the manifolds 224 and 226 includes muffling elements. As such, at least one of the manifolds 224 and 226 includes, is associated with, or functions as part of, flow collectors and/or integrated mufflers. The cross-over conduits 440 can also be associated, or function as part of, the flow collectors and/or integrated mufflers.

As shown in FIGS. 3 and 4, the compressor 200 is provided with outlet ports 442. In the illustrated examples, there are four outlet ports 442 corresponding to two suction ports and two exhaust ports. Configuration of the outlet ports 442 can vary. For example, the outlet ports 442 can be at either end of the compressor 200, at various radial locations, or any combinations thereof. In some examples, the outlet ports 442 are integrally formed with other components of the compressor 200, such as by molding or casting.

Figure 14:
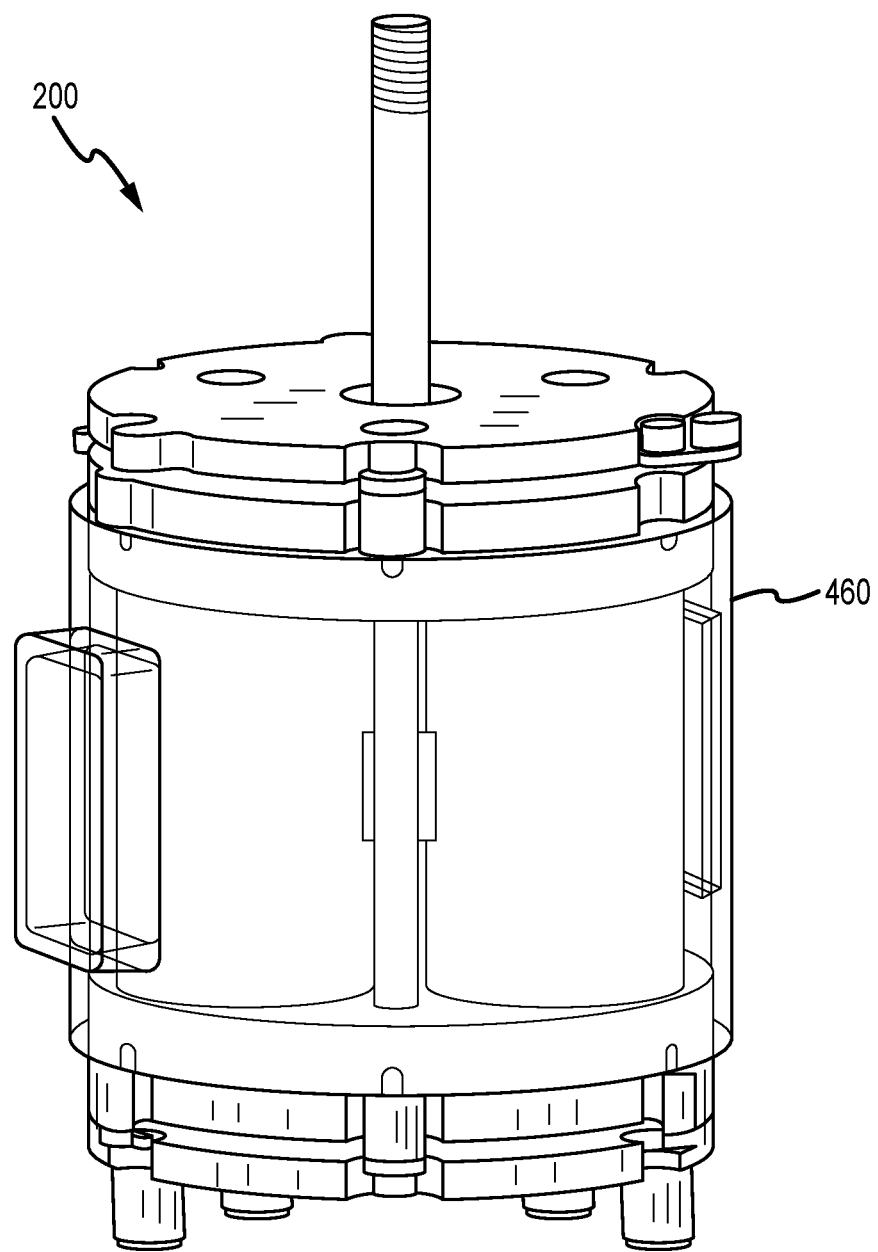
FIG. 14 schematically illustrates a cooling device for the compressor.

FIG. 14 schematically illustrates a cooling device 460 for the compressor 200. The cooling device 460 can be designed for cylinder head cooling. Since the components (e.g., the cylinders 250) between the first and second manifolds 224 and 226 are independently disposed and spaced apart from one another, the compressor 200 has an increased surface area that can be cooled from the inside of the compressor 200. The cylinder arrangement in the present disclosure exposes the inner diameter and the outer diameter of the cylinders (which are for example made of aluminum), thereby enabling internal cooling. In some examples, the cooling device 460 includes a shroud configured to force cooling gases through the compressor 200, instead of around the compressor 200. The cooling device 460, which provides such internal cooling, can impinge air flow to improve cooling of the pressure cylinders. Since cooling is provided from the inside, the cooling device 460 can also reduce the system package size and weight. Such internal cooling also allows using plastic manifolds.

As described herein, the illustrated example of the compressor 200 includes three cylinders 250, each of which provides two cylinder heads defined by the opposite piston heads of the piston assemblies 270. One of the cylinders 250 is used to produce positive pressure flow, and the other two cylinders 250 are used to produce negative pressure flow. The compressor 200 can be easily configured for various ratios. Alternatively, all of the heads of the compressor 200 are configured to produce the same output type. In some examples, the ratios can be fine-tuned by asymmetrical bore diameters. In other examples, the ratios are adjusted by asymmetrical distances from the axis of rotation A of the drive shaft 210. For example, at least one of the cylinder assemblies can be spaced apart from the axis of rotation A of the drive shaft 210 differently than the other cylinder assemblies, thereby providing a different piston stroke.

As described above, the compressor in accordance with the present disclosure can employ a double-headed piston and a single-piece cylinder for the piston. This configuration eliminates bulky multi-part cylinder arrangements which require high tolerance alignment between pistons and cylinders (e.g., in the X and Y directions on a plane a longitudinal axis of the pistons and cylinders transverses).

Further, the piston and cylinder configuration of the present disclosure enables the compact and lightweight pancake manifolds (i.e., the first and second manifolds 224 and 226), which provide cylinder mounting surfaces that control the cylinder alignment in the Z direction (i.e., the longitudinal axis of the piston and cylinder). Such improved Z direction alignment of the piston and cylinder reduces dead volume within compression chambers in the cylinder.

As such, the compressor of the present disclosure provides a light-weight, low cost, and low noise compressor and an oxygen concentrator using the same.

Although the compressor of the present disclosure is primarily described to be used with an oxygen concentrator, the compressor can be also used in various applications. Examples of such applications include a medical ventilator, a nitrogen concentrator, a natural gas compressor, a cryocooler compressor, an aeration pump for water treatment, scientific equipment, and air compressor/vacuum pumps for multiple purposes.

A medical ventilator is a mechanical ventilator designed to move breathable air into and out of the lungs, and to provide breathing for a patient who is physically unable to breathe or breathing insufficiently. The compressor of the present disclosure can be used in such a medical ventilator to provide compressed air.

A nitrogen concentrator or generator can be used to concentrate nitrogen for various uses, such as for beverages. Nitrogen concentrators can be configured and operated similarly to an oxygen concentrator as described herein.

A natural gas compressor is a device for increasing the pressure of a natural gas by reducing its volume. The compressor of the present disclosure can be configured and used for such a natural gas compressor.

A cryocooler is a cooler for cooling some particular application to cryogenic temperatures. One example of cryocoolers is Gifford-McMahon (GM) coolers, which can be used in many low-temperature systems, such as MM and cryopumps. At least some embodiments of GM coolers include a compressor, which can be implemented by the compressor of the present disclosure. Another example of cryocoolers is Joule-Thomson (JT) coolers. At least some embodiments of JP coolers include a compressor, and the compressor of the present disclosure can be used for that purpose.

The compressor of the present disclosure can also be used for aeration pumps for various purposes (e.g., water treatment), which use oxygen or ozone.

Scientific equipment can also employ the compressor of the present disclosure. Such scientific equipment includes gas analyzers and other suitable scientific or research equipment.

Air compressor/vacuum pumps can be implemented by the compressor of the present disclosure for multiple purposes, such as dental, food preparation, pharmaceutical manufacturing, paint spray, general shop air service, and other suitable purposes.

FIG. 19 is a schematic cross sectional view of another exemplary embodiment of the compressor 200. In this embodiment, the compressor 200 does not include a universal joint as the wobble anti-rotation device 400 as illustrated in, for example, FIG. 4. Instead, as illustrated in, for example, FIGS. 16, 17, and 20, the compressor 200 includes another wobble anti-rotation mechanism for the wobble plate assembly, such as the shoe 472 and associated components as described herein. Further, the compressor 200 in FIG. 19 can include one or more piston anti-rotation mechanisms, as described herein.

One example of the piston anti-rotation mechanisms includes the posts 482 and the flanges 502 of the hub plate 302, as described above. The posts 482 and/or the hub plate 302 (at least the flanges 502 thereof) can be made of a material that incorporates dry lubricant. In some embodiments, the posts 482 and/or the hub plate 302 (at least the flanges 502 thereof) are made of a polymer material compounded with at least one of graphite, PTFE, bronze, and other materials. The polymer material can be polyimide (PI), Polyetheretherketone (PEEK), or other thermoplastic materials. One example of such compounded material is one of the VICTREX PEEK polymers, such as 450FC30. In other embodiments, the posts 482 and/or the hub plate 302 (at least the flanges 502 thereof) can be made of a material that incorporates a polyimide compounded with graphite. Examples of such a compound include Vespel materials, such as Vespel SP-22, manufactured by DuPont (Delaware, U.S.A.). In addition or alternatively, the posts 482 and/or the hub plate 302 (at least the flanges 502 thereof) can be coated with a layer of wear resistant and low friction materials, such as a fluoropolymer-based coating material. One example of the fluoropolymer material is available from Whitford, such as Xylan 1000 series or Xylan 8100 series. Other materials can also be used for such coating.

Referring to FIGS. 21-22 and 24-25, another example of the piston anti-rotation mechanisms is illustrated. In this example, a piston guide block or plug 520 is provided to guide the axial movement of the piston assembly 270 within the cylinder 250 and prevent the rotation of the piston assembly 270 relative to the cylinder 250. In some embodiments, the piston guide plug 520 is inserted through a hole 510 of the cylinder 250 and engages with an axial slot 512 defined in the post 482. The hole 510 of the cylinder 250 is shaped to correspond to the shape of the piston guide plug 520 such that the piston guide plug 520 is fixed with respect to the cylinder 250. In the illustrated example, a fastener (e.g., a screw) 524 is used to mount the piston guide plug 520 to the cylinder 250. In other examples, other methods, such as gluing, can be used to mount the piston guide plug 520 to the cylinder 250.

The piston guide plug 520 is arranged to extend into the slot 512 of the post 482 of the piston assembly 270 and thus guides the movement of the piston assembly 270 as the piston assembly 270 axially moves within the cylinder 250. The slot 512 extends axially and has a width that corresponds to, or slightly larger than, the size of the piston guide plug 520. Therefore, the piston guide plug 520 is laterally constrained within the slot 512, and thus the slot 512 can limit or prevent the piston assembly 270 from rotating about its own axis as the piston assembly 270 axially moves within the cylinder 250.

In this example, the piston guide plug 520 is configured to oval in cross section. Other shapes are also possible in other examples.

In some embodiments, the piston guide plug 520 is made of the same material as the post 482 and/or the cylinder 250.

In some embodiments, the piston guide plug 520 can be made of a material that incorporates dry lubricant. In some embodiments, the piston guide plug 520 is made of a polymer material compounded with at least one of graphite, PTFE, bronze, and other materials. The polymer material can be polyimide (PI), Polyetheretherketone (PEEK), or other thermoplastic materials. One example of such compounded material is one of the VICTREX PEEK polymers, such as 450FC30. In other embodiments, the piston guide plug 520 can be made of a material that incorporates a polyimide compounded with graphite. Examples of such a compound include Vespel materials, such as Vespel SP-22, manufactured by DuPont (Delaware, U.S.A.). In addition or alternatively, the piston guide plug 520 can be coated with a layer of wear resistant and low friction materials, such as a fluoropolymer-based coating material. One example of the fluoropolymer material is available from Whitford, such as Xylan 1000 series or Xylan 8100 series. Other materials can also be used for such coating.

In some embodiments, the bearing element 308 of the wobble plate assembly 260 can be configured as a plurality of bearings. In the illustrated example of FIG. 23, the bearing element 308 includes two bearings 540 and 542, which can be assembled to the hub plate 402 and the drive shaft 210 similarly as described in FIG. 4.

In some embodiments, the shaft sleeve 320 and the bearing element 308 are arranged such that a center C of two bearings 540 and 542 is located at the intersection of the axis of rotation A of the drive shaft 210 and the longitudinal axis A3 of the eccentric stub shaft 322 of the shaft sleeve 320. This arrangement can ensure the wobble plate assembly 260 to move as desired. In other embodiments, other configurations may be also possible.

As described herein, the wobble plate compressor according to the present disclosure can be configured as a dry compressor that uses dry lubricants in various locations. The wobble plate compressor of the present disclosure can eliminate use of viscous lubricants (e.g., oil or grease) in various parts of the compressor. In some embodiments, such parts of the compressor are made of, or coated with, materials that do not require viscous lubricants, as described throughout this document. For example, the connecting rod 350, 352 and the spherical element 304 are made of or coated with low friction materials, and configured as described herein, so that viscous lubricant is not required at the interface therebetween. Further, the connecting rod 350, 352 and the piston head 340, 342 are made of or coated with low friction materials, and configured as described herein, so that they can operate without viscous lubricant at the interface. Moreover, in some examples, the piston head 340, 342 and the cylinder 250 are made of or coated with low friction materials, so that the piston head 340, 342 is reciprocatingly received within the cylinder 250 without viscous lubricant between the outer diameter of the piston head 340, 342 and the cylinder wall (e.g., the inner diameter of the cylinder 250). The wobble anti-rotation structures and the piston anti-rotation structures as described herein are also some of the examples that allow the compressor to be free of viscous lubricant.

The various examples and teachings described above are provided by way of illustration only and should not be construed to limit the scope of the present disclosure. Those skilled in the art will readily recognize various modifications and changes that may be made without following the example examples and applications illustrated and described herein, and without departing from the true spirit and scope of the present disclosure.

What is claimed is:

1. A wobble plate compressor comprising:
a motor that rotates an axle around an axis of rotation;
a wobble plate having at least one substantially spherical distal attachment member, the wobble plate coupled to the axle so that the distal attachment member reciprocates upon rotation of the axle;
a double-headed single piece piston assembly, where the double-headed single piece piston assembly is comprised of two compression faces fixedly connected so as to substantially prevent movement of one of the two compression faces independently of the other; and
at least one single-piece cylinder receiving the double-headed single piece piston to define two compression chambers, the cylinder including a window through which the wobble plate engages with the piston assembly such that the distal attachment member penetrates the piston assembly and engages two opposing connecting rods whereby the piston assembly reciprocates within the cylinder along a second axis parallel to the axis of rotation upon rotation of the axle and the distal attachment member reciprocates on a path that includes a portion with a transverse component relative to the second axis, wherein each of the two opposing connecting rods has a concave portion configured to engage the substantially spherical distal attachment member of the wobble plate and wherein each of the two opposing connecting rods has a connecting rod interface portion configured to slidably interface with a respective piston head of the double-headed single piece piston during reciprocation.

2. The wobble plate compressor of claim 1, further comprising a wobble plate anti-rotation device configured to prevent rotation of the wobble plate.

3. The wobble plate compressor of claim 2, wherein the wobble plate anti-rotation device includes a shoe pivotally coupled to the wobble plate and configured to slide against an exterior of the at least one cylinder.

4. The wobble plate compressor of claim 1, further comprising a piston anti-rotation device configured to prevent rotation of the double-headed piston assembly relative to the cylinder.

5. The wobble plate compressor of claim 4, wherein the piston anti-rotation device includes a flange provided to the wobble plate and configured to slide against a portion of the double-headed piston.

6. The wobble plate compressor of claim 5, wherein the portion of the double-headed piston includes a post extending between opposite heads of the double-headed single piece piston assembly.

7. The wobble plate compressor of claim 4, wherein the piston anti-rotation device includes a piston guide plug engaging with an axial slot of the double-headed piston and being laterally constrained within the axial slot.

8. The wobble plate compressor of claim 1, wherein an interface portion of the piston head, which interfaces with the connecting rod interface portion, is concave and the connecting rod interface portion is convex.

9. The wobble plate compressor of claim 1, wherein an interface portion of the piston head, which interfaces with the connecting rod interface portion, is convex and the connecting rod interface portion is concave.

10. The wobble plate compressor of claim 8, further comprising an assembly tool configured to temporarily adjust the connecting rods at a predetermined arrangement with respect to the distal attachment member of the wobble plate.

11. The wobble plate compressor of claim 1, wherein the wobble plate compressor is at least partially made of a material that incorporates dry lubricant.

12. The wobble plate compressor of claim 1, wherein the at least one cylinder includes at least one vacuum cylinder or at least one pressure cylinder.

13. The wobble plate compressor of claim 1, wherein the at least one cylinder includes at least two vacuum cylinders and one pressure cylinder.

14. The wobble plate compressor of claim 1, wherein the wobble plate is attached to the axle via at least one bearing at an angle relative to the axle to orbitally tilt around the axis of rotation.

15. The wobble plate compressor of claim 1, wherein the distal attachment member reciprocates substantially in a three-dimensional orbit defined substantially along the second axis.

16. An oxygen concentrator comprising: a concentrator; and a wobble plate compressor including: a motor that rotates an axle around an axis of rotation; a wobble plate having at least two balls, each ball on a different distal portion of the wobble plate, the wobble plate coupled to the axle so that each ball reciprocates upon rotation of the axle; a double-headed single piece piston, where the double-headed single piece piston is comprised of two compression faces fixedly connected so as to substantially prevent movement of one of the two compression faces independently of the other; and at least one single-piece cylinder receiving the double-headed single piece piston assembly to define two compression chambers, the cylinder including a window through which the wobble plate engages with the double-headed single piece piston such that the double-headed single piece piston is attached to an associated one of the balls whereby the double-headed single piece piston reciprocates within the cylinder upon the rotation of the axle and the ball reciprocates on a path that includes a portion with a transverse component relative to the second axis, wherein each double-headed single piece piston includes two opposing rods that engage its associated ball on the wobble plate, and wherein each of the two opposing connecting rods has a concave portion configured to engage the substantially spherical distal attachment member of the wobble plate and wherein each of the two opposing connecting rods has a connecting rod interface portion configured to slidably interface with a respective piston head of the double-headed single piece piston during reciprocation.

17. The oxygen concentrator of claim 16, wherein an interface portion of the piston head, which interfaces with the connecting rod interface portion, is concave and the connecting rod interface portion is convex.

18. The oxygen concentrator of claim 16, wherein the wobble plate is attached to the axle via at least one bearing at an angle relative to the axle to orbitally tilt around the axis of rotation.

19. The oxygen concentrator of claim 16, wherein the concentrator is a pressure swing absorption concentrator.

20. The oxygen concentrator of claim 16, wherein the concentrator is a vacuum pressure swing absorption concentrator.

21. The oxygen concentrator of claim 16, wherein the ball reciprocates substantially in a three-dimensional orbit defined substantially along an axis of the cylinder.

* * * * *